US011452514B2

(12) United States Patent
Truckey et al.

(10) Patent No.: US 11,452,514 B2
(45) Date of Patent: Sep. 27, 2022

(54) RETRACTOR SYSTEM AND SIDE LOAD CONNECTOR FOR SURGICAL RETRACTOR BLADE

(71) Applicant: Thompson Surgical Instruments, Inc., Traverse City, MI (US)

(72) Inventors: Adam Truckey, Suttons Bay, MI (US); Daniel K. Farley, Traverse City, MI (US); Steven Nowak, Traverse City, MI (US); Christopher T. Martin, Cedar, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 168 days.

(21) Appl. No.: 16/817,810

(22) Filed: Mar. 13, 2020

(65) Prior Publication Data
US 2020/0214686 A1    Jul. 9, 2020

Related U.S. Application Data

(63) Continuation of application No. PCT/US2018/047164, filed on Aug. 21, 2018.
(Continued)

(51) Int. Cl.
*A61B 17/02* (2006.01)
*A61B 17/00* (2006.01)

(52) U.S. Cl.
CPC .... *A61B 17/0206* (2013.01); *A61B 2017/00407* (2013.01); *A61B 2017/00477* (2013.01)

(58) Field of Classification Search
CPC ........... A61B 17/0206; A61B 17/02; A61B 2017/00477
See application file for complete search history.

(56) References Cited

U.S. PATENT DOCUMENTS

| 4,971,038 A | 11/1990 | Farley |
| 5,520,610 A | 5/1996 | Giglio et al. |

(Continued)

FOREIGN PATENT DOCUMENTS

| EP | 1269922 | 1/2013 |
| ES | 2272170 | 4/2007 |
| FR | 2690067 | 10/1993 |

OTHER PUBLICATIONS

International Preliminary Report on Patentability for PCT/US2018/047164, dated Apr. 2, 2020, 19 pages.
(Continued)

*Primary Examiner* — Nicholas J Plionis
(74) *Attorney, Agent, or Firm* — McAndrews, Held & Malloy, Ltd.

(57) ABSTRACT

A retractor system includes a retractor blade and a retractor arm having a side-load connector. The side-load connector includes a port that passes through an upper surface and a lower surface of the side-load connector. A sidewall opening in the side-load connector permits lateral passage of the attachment post through a sidewall to the port. The side-load connector includes a cam pivotably coupled between the lower surface and the upper surface and a spring that applies a biasing force on the cam. The biasing force biases the cam to a closed position in which the cam extends into the opening and prevents unloading the attachment post from the port via the opening. The cam selectively engages either a first groove or a second groove of the attachment post sidewall. The side-load connector further includes teeth that engage teeth of the retractor body when the cam engages the first groove.

14 Claims, 19 Drawing Sheets

Related U.S. Application Data

(60) Provisional application No. 62/560,009, filed on Sep. 18, 2017, provisional application No. 62/560,034, filed on Sep. 18, 2017.

(56) References Cited

U.S. PATENT DOCUMENTS

| | | | |
|---|---|---|---|
| 5,902,233 | A | 5/1999 | Farley et al. |
| 5,984,865 | A * | 11/1999 | Farley ............... A61B 17/02 600/213 |
| 5,984,867 | A | 11/1999 | Deckman et al. |
| 6,042,540 | A * | 3/2000 | Johnston ......... A61B 17/0206 600/219 |
| 6,468,207 | B1 | 10/2002 | Fowler |
| 6,733,444 | B2 | 5/2004 | Phillips |
| 6,860,850 | B2 | 3/2005 | Phillips et al. |
| 7,569,014 | B2 | 8/2009 | Bass et al. |
| 8,257,255 | B2 | 9/2012 | Farley et al. |
| 8,357,087 | B2 | 1/2013 | Fetzer |
| 8,360,971 | B2 | 1/2013 | Farley et al. |
| 8,974,381 | B1 | 3/2015 | Lovell et al. |
| 9,113,853 | B1 | 8/2015 | Casey et al. |
| 9,216,016 | B2 | 12/2015 | Fiechter et al. |
| 9,386,916 | B2 | 7/2016 | Predick et al. |
| 2004/0249388 | A1 | 12/2004 | Michelson |
| 2006/0178566 | A1 | 8/2006 | Fetzer |
| 2007/0055109 | A1 * | 3/2007 | Bass ............... A61B 17/02 600/234 |
| 2007/0270840 | A1 | 11/2007 | Chin et al. |
| 2012/0271118 | A1 * | 10/2012 | White ............. A61B 17/02 600/226 |
| 2015/0182211 | A1 * | 7/2015 | Nowak ......... A61B 17/0206 600/215 |
| 2015/0250467 | A1 * | 9/2015 | Higgins ......... A61B 17/025 600/215 |
| 2018/0271509 | A1 * | 9/2018 | Truckey ....... A61B 17/0218 |

OTHER PUBLICATIONS

International Search Report and Written Opinion for PCT/US2018/047164, dated Nov. 9, 2018, 21 pages.

\* cited by examiner

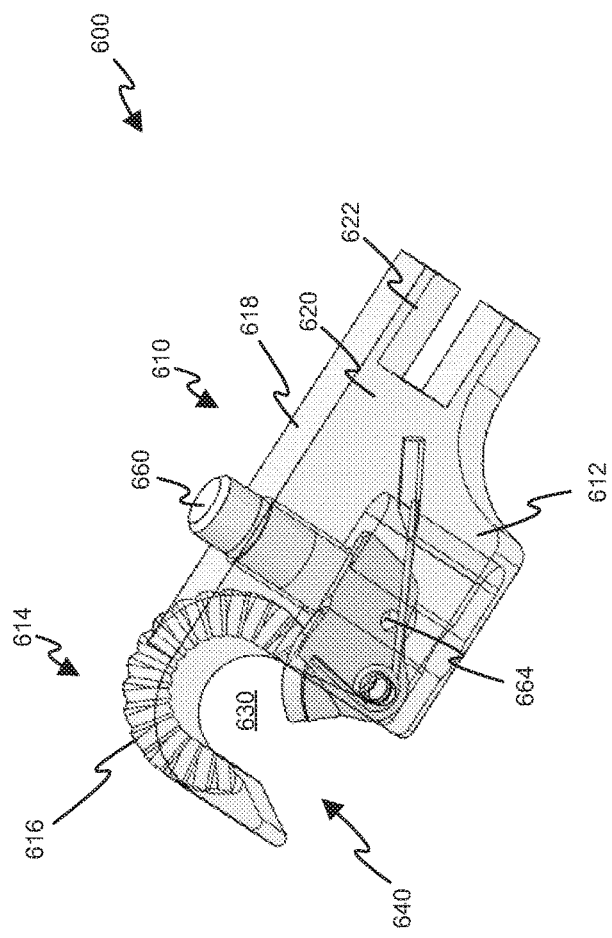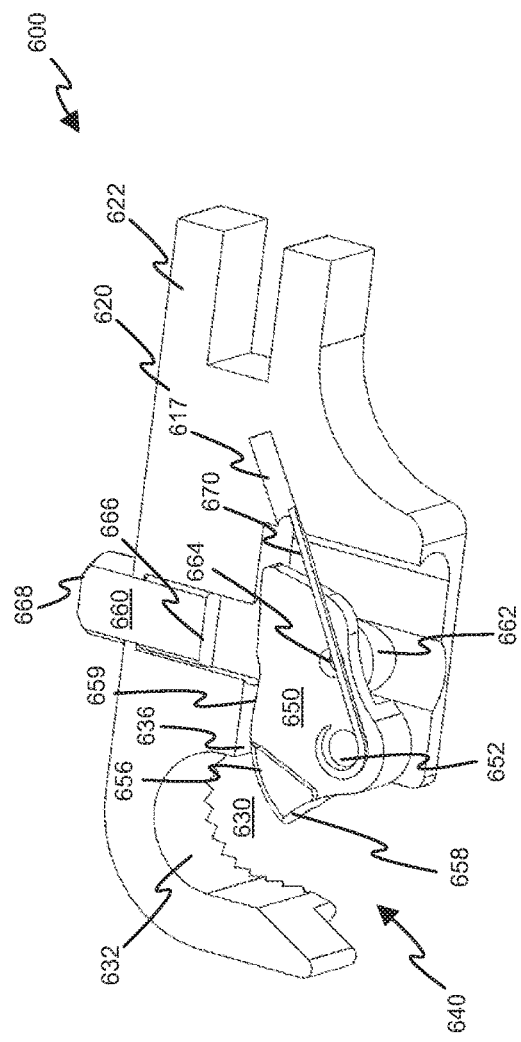
FIG. 6A
FIG. 6B

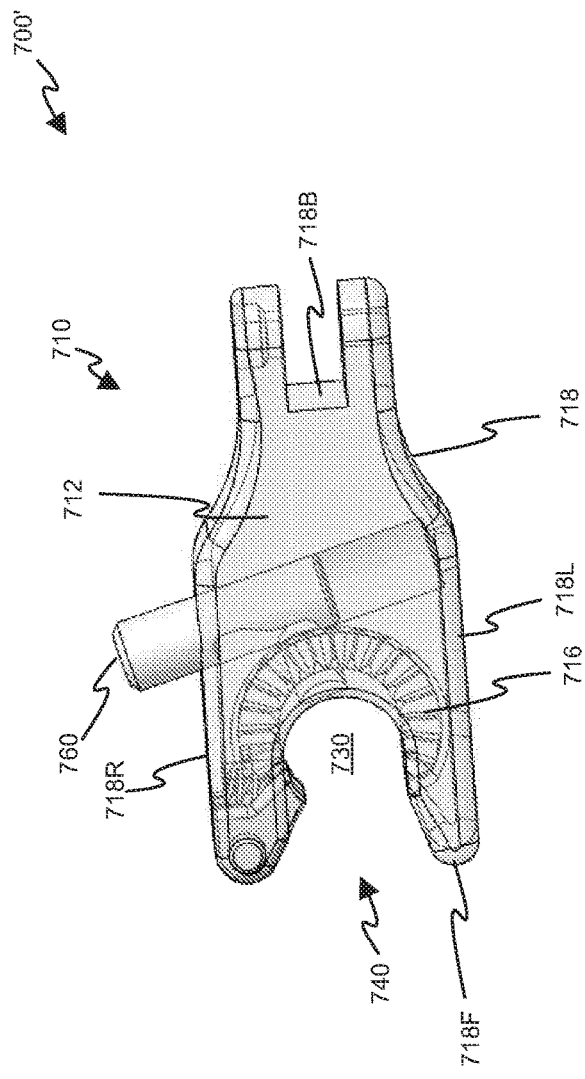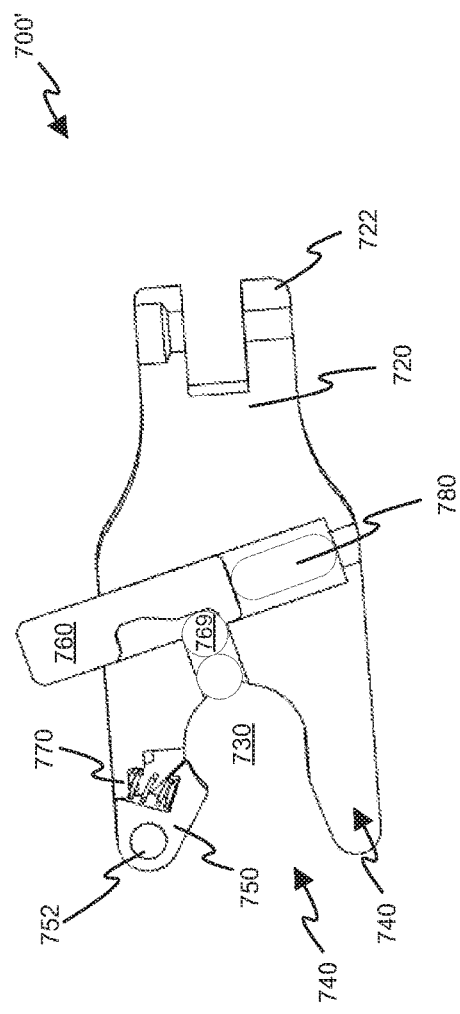
FIG. 9A
FIG. 9B

RETRACTOR SYSTEM AND SIDE LOAD CONNECTOR FOR SURGICAL RETRACTOR BLADE

RELATED APPLICATIONS

This application is a continuation of PCT Application No. PCT/US2018/047164, having a filing date of Aug. 21, 2018, which claims benefit and priority to U.S. Provisional Patent Application No. 62/560,034, having a filing date of Sep. 18, 2017 and U.S. Provisional Patent Application No. 62/560,009, having a filing date of Sep. 18, 2017, the contents of each of above-identified applications is hereby incorporated herein by reference in their entirety.

BACKGROUND

The present disclosure relates to a surgical apparatus that retracts soft tissue and other anatomy of a patient in order to provide access to an operative site.

During a surgical procedure, a surgeon may make an incision in a patient to access internal organs, bones, and/or other anatomical structures. Retraction devices may be used to hold back soft tissue and other patient anatomy in the immediate area of the incision. Such retraction devices may provide the surgeon with an unobstructed view of the internal organs, bones, and/or other anatomical structures. Furthermore, the retraction devices may provide the surgeon with an opening via which the surgeon may access the anatomical structures with one or more surgical tools.

Further limitations and disadvantages of conventional and traditional approaches will become apparent to one of skill in the art, through comparison of such approaches with the present disclosure as set forth in the remainder of the present application with reference to the drawings.

SUMMARY

Various aspects of this disclosure provide a retractor system comprising retractors that retract anatomy to provide exposure of an operative site. For example and without limitation, various aspects of the disclosure are directed to a surgical retractor arm that permits side loading a surgical retractor blade to the arm. Certain aspects of the disclosure are further directed to a swivel lock aspect. The swivel lock aspect generally provides an unlocked state in which a side-loaded surgical retractor blade is permitted to rotate or swivel with respect to a retractor arm and a locked state in which the side-loaded surgical retractor blade is prevented from rotating or swiveling with respect to the retractor arm. Yet further aspects of the disclosure are directed to an angle adjustment assembly that angles a retractor without causing the retractor to dive further into the incision.

BRIEF DESCRIPTION OF THE DRAWINGS

FIGS. 6A-6B depict a second embodiment for a side-load connector of the retractor system of FIGS. 1A-1C.

FIGS. 9A-9B depict a fifth embodiment for a side-load connector of the retractor system of FIGS. 1A-1C.

DETAILED DESCRIPTION

Figure 1A:
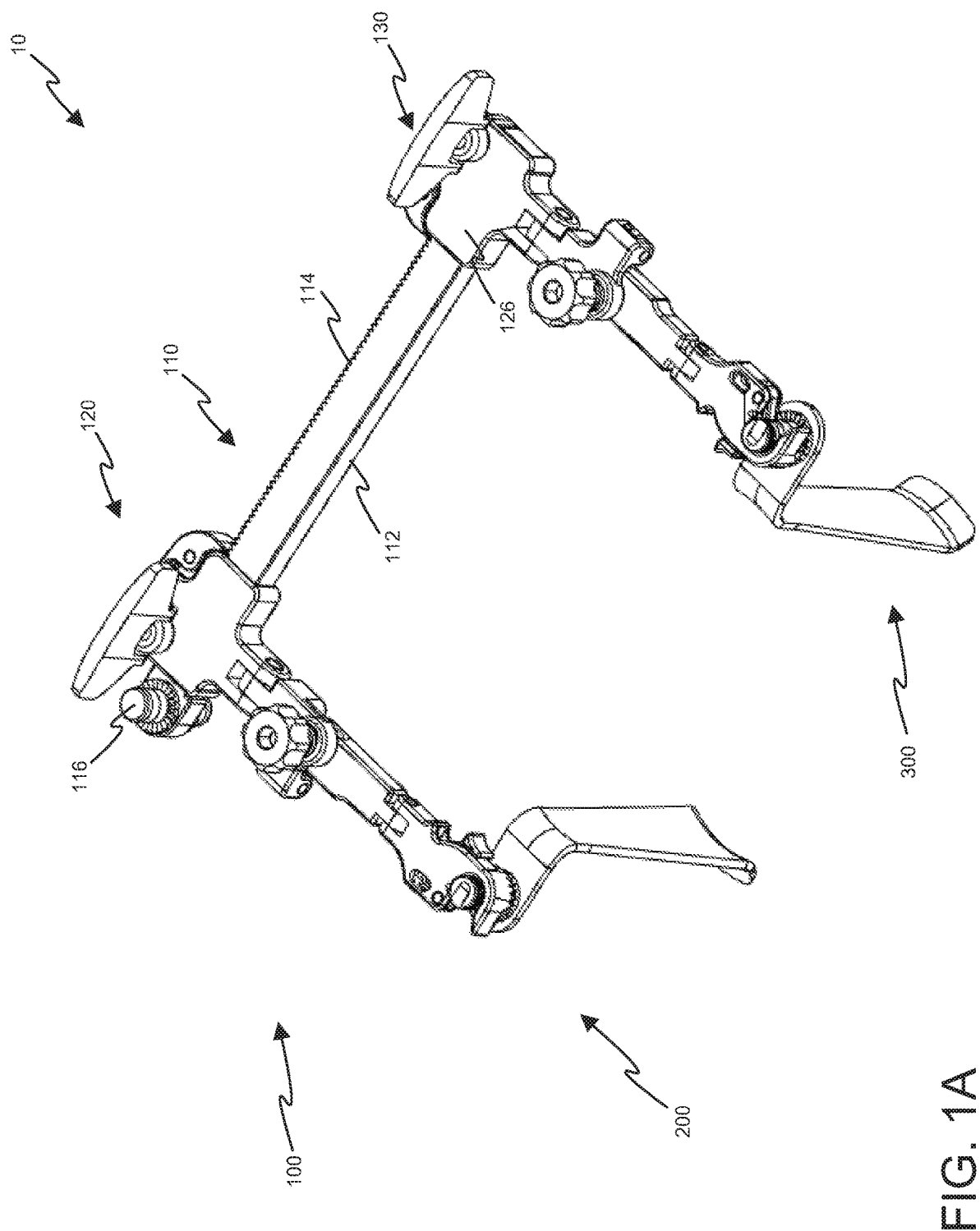
FIGS. 1A-1C depict a retractor system in accordance with various aspects of the present disclosure.

The following discussion presents various aspects of the present disclosure by providing examples thereof. Such examples are non-limiting, and thus the scope of various aspects of the present disclosure should not necessarily be limited by any particular characteristics of the provided examples. In the following discussion, the phrases "for example," "e.g.," and "exemplary" are non-limiting and are generally synonymous with "by way of example and not limitation," "for example and not limitation," and the like.

As utilized herein, "and/or" means any one or more of the items in the list joined by "and/or". As an example, "x and/or y" means any element of the three-element set $\{(x), (y), (x, y)\}$. In other words, "x and/or y" means "one or both of x and y." As another example, "x, y, and/or z" means any element of the seven-element set $\{(x), (y), (z), (x, y), (x, z), (y, z), (x, y, z)\}$. In other words, "x, y and/or z" means "one or more of x, y, and z."

The terminology used herein is for the purpose of describing particular examples only and is not intended to be limiting of the disclosure. As used herein, the singular forms are intended to include the plural forms as well, unless the context clearly indicates otherwise. It will be further understood that the terms "comprises," "includes," "comprising," "including," "has," "have," "having," and the like when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present disclosure. Similarly, various spatial terms, such as "upper," "lower," "side," and the like, may be used in distinguishing one element from another element in a relative manner. It should be understood, however, that components may be oriented in different manners, for example a semiconductor device may be turned sideways so that its "top" surface is facing horizontally and its "side" surface is facing vertically, without departing from the teachings of the present disclosure.

In the drawings, various dimensions (e.g., layer thickness, width, etc.) may be exaggerated for illustrative clarity. Additionally, like reference numbers are utilized to refer to like elements through the discussions of various examples.

The discussion will now refer to various example illustrations provided to enhance the understanding of the various aspects of the present disclosure. It should be understood that the scope of this disclosure is not limited by the specific characteristics of the examples provided and discussed herein.

Figure 1B:
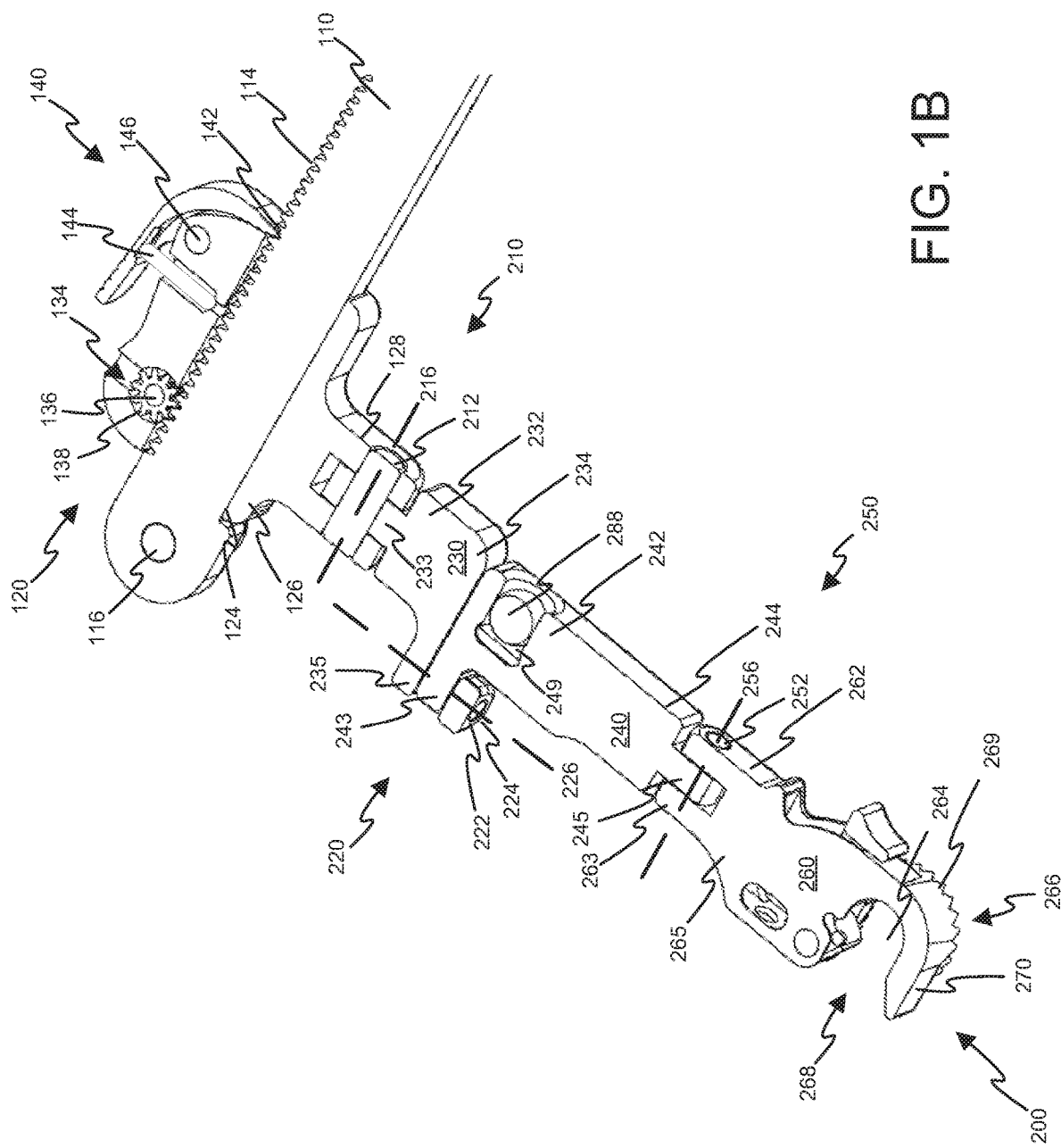
Figure 1C:
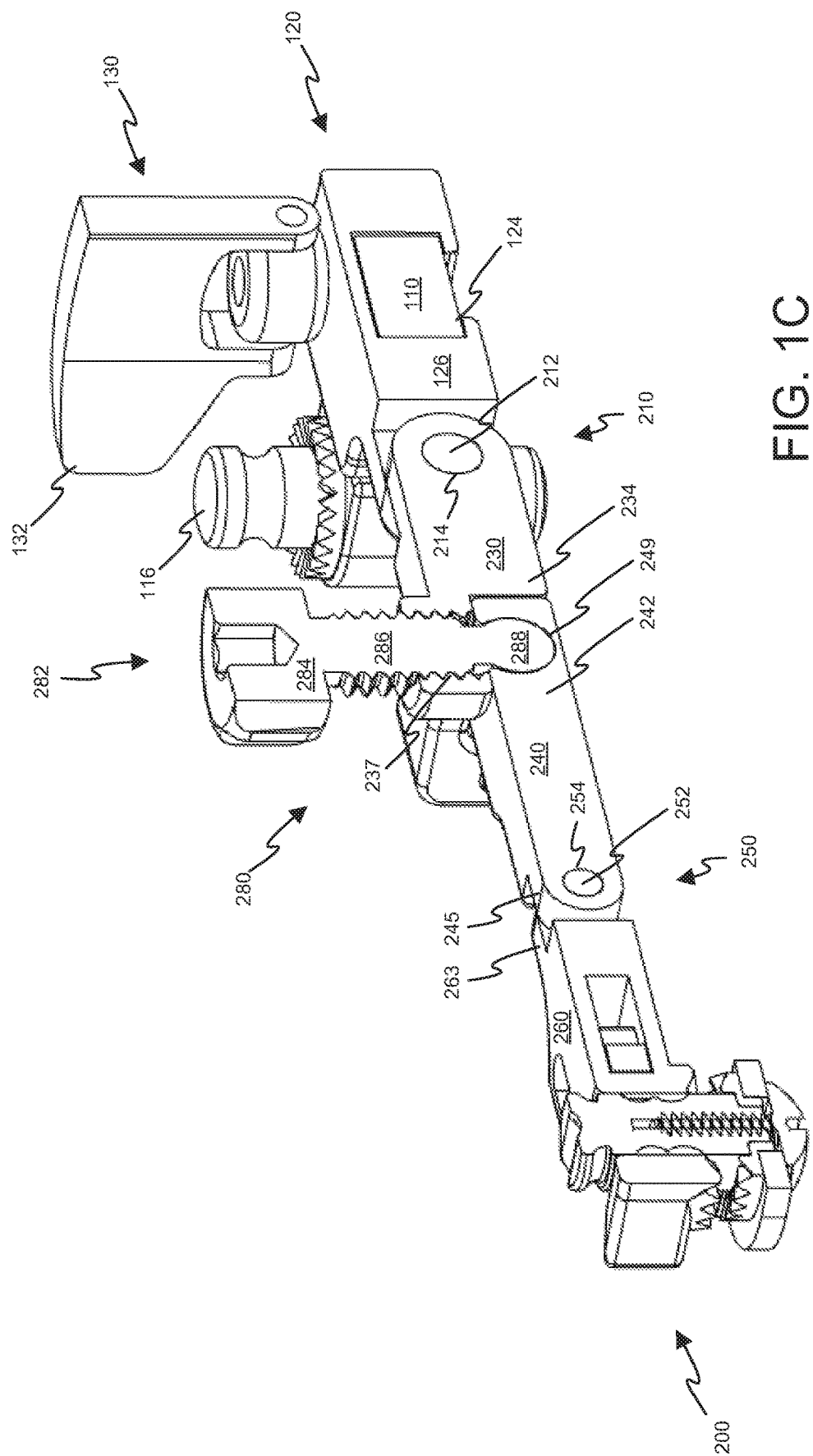

Referring now to FIGS. 1A-C, perspective and cross-sectional views of an embodiment of a retractor system 10 are presented. As shown, the retractor system 10 may include a self-retaining retractor 100 and surgical retractor blades 300. The self-retaining retractor system 100 may further include one or more handle assemblies 400 shown in FIGS. 4A-C. The handle assemblies 400 may permit a practitioner to more easily manipulate and position the surgical retractor blades 300.

The self-retaining retractor 100 may include a crossbar 110 and first and second retractor arms 200. In various embodiments, one or more parts of the self-retaining retractor system 10 may be formed from surgical stainless steel. Other embodiments may utilize various alternative materials to form all or part of self-retaining retractor system 10.

As shown, the crossbar 110 may comprise a cylindrical rod or rail 112 having a rectangular cross section. Moreover, the rail 112 may include teeth 114 spanning a longitudinal side of the rail 112. The rail 112 may further include an attachment post 116. As shown, the attachment post 116 may be positioned toward an end of the rail 112 to permit securing of the retractor 100 to a frame assembly or operating table (not shown). The attachment post 116 may operate in a similar manner to the attachment post of the surgical blades 300, which is described in detail below.

The retractor arms 200 may be coupled to the crossbar 110 via respective ratchets 120. The ratchets 120 may engage the teeth 114 of the crossbar 110 to impart ratcheted-movement of the retractor arms 200 along crossbar 110, thus permitting the retractor arms 200 to traverse the crossbar 110. To this end, the crossbar 110 may pass through a longitudinal aperture 124 in a base portion 126 of each ratchet 120. The ratchet 120 further includes a crank 130 having an handle 132 and a gear 134.

Referring now to FIG. 1B, axel 136 positions the gear 134 such that its teeth 138 engage teeth 114 of the crossbar 110. Rotation of the handle 132 imparts rotation of the gear 134 about the axel 136 causing the teeth 138 to advance along the crossbar 110 thus causing the ratchet 120 and attached arm 200 to traverse the crossbar 110.

The ratchets 120 may further include a spring-biased lever 140 having a pawl 142 that selectively engages teeth 114 of the crossbar 110. In particular, a spring 144 biases the lever 140 such that the pawl 142 engages the teeth 114 when no external pressure is applied to the lever 140. Conversely, when sufficient pressure is applied to the lever 140 to overcome the spring bias, the lever 140 rotates about pin 146, thus causing the pawl 142 to move away from and disengage the teeth 114. In one embodiment, the pawl 142 and teeth 114 are angled to permit ratcheted movement in one direction while preventing movement in the opposite direction when the pawl 130 is engaged with the teeth 114. To this end, the teeth 114 of the crossbar 110 in one embodiment are uniformly-shaped and symmetrically-sloped, with leading and trailing edges having the same slope. However, the pawl 142 is not symmetrically sloped. Instead, the leading edge (i.e., edge toward the direction of ratcheted movement) is more moderately-sloped than the opposite trailing edge. As a result of the more moderately-sloped or less steeply-sloped leading edge, lateral movement of the ratchet 120 with respect to the crossbar 110 in the desired ratcheted direction imparts an upward force upon the pawl 142 that is sufficient to overcome the biasing force of the spring 144, thus permitting the pawl 142 to travel over the teeth 114. Conversely, as a result of the more steeply-sloped trailing edge, lateral movement of the ratchet 120 with respect to the crossbar 110 in the opposite direction fails to impart an upward force upon the pawl 142 that is sufficient to overcome the biasing force of the spring 144, thus preventing the pawl 142 from traveling over the teeth 114. In this manner, the ratchet 120 may lock or retain its attached retractor arms 200 to a particular location along the crossbar 110, thereby maintaining a desired retraction force upon soft tissue in contact with the retractor blades 300.

Thus, each retractor arm 200, via its respective ratchet 120, may traverse the crossbar 110 in a ratcheted-manner in first or retraction direction away from the other retractor arm 200. Moreover, by pressing the release lever 140, a practitioner may disengage the pawl 142 thus permitting movement of the respective arm 200 along the crossbar 110 via non-ratcheted manner in a second direction that is opposite the retraction direction and toward the other retractor arm 200.

As shown in FIGS. 1A-C, each retractor arm 200 may each include multiple arm portions. In particular, each retractor arm 200 may include a proximal arm portion 230 and a distal arm portion 240. Each proximal arm portion 230 may include a proximal end 232 pivotably coupled to a base portion 126 of a respective ratchet 120 via a hinge 210. Each hinge 210 may comprise a pin 212, one or more barrels 128 of the base portion 126, and one or more barrels 233 of the proximal arm portion 230. The barrels 128 may interleave with the barrels 233 and define a longitudinal aperture 214. Each pin 212 may pass through a respective aperture 214 defined by barrels 128, 233, thereby pivotally coupling the proximal end 232 of a proximal arm portion 230 to its respective base portion 126.

Each hinge 210 may further provide a pivot axis 216 about which the proximal arm portion 230 may pivot. As shown, the hinges 210 may provide pivot axes 216 that are coplanar with and parallel to crossbar 110. In other embodiments, the hinges 210 may orient pins 212 and barrels 128, 233 such that each axis 216 is not coplanar with and/or is not parallel to crossbar 110. Furthermore, while FIG. 1 depicts each pivot axis 216 as having the same orientation with respect to the crossbar 110, in some embodiments, the hinges 210 may distinctly orient the pivot axes 216 with respect to the crossbar 110 so as to provide pivot axes 216 that are oriented differently from one another.

A proximal end 242 of each distal arm portion 240 may be pivotably coupled to a distal end 234 of its respective proximal arm portion 230 via a hinge 220. Each hinge 220 may comprise a pin 222, one or more barrels 235 of the proximal arm portion 230, and one or more barrels 243 of the distal arm portion 240. The barrels 235 may interleave with the barrels 243 and define a longitudinal aperture 224. Each pin 222 may pass through a respective aperture 224 defined by barrels 235, 243, thereby pivotally coupling distal ends 234 of the proximal arm portions 230 to respective proximal ends 242 of the distal arm portions 240.

As shown, each hinge 220 may provide a pivot axis 226 about which the distal arm portion 240 may pivot. As shown, the hinges 220 may provide pivot axes 226 that are perpendicular to crossbar 110. In other embodiments, the hinges 220 may orient pins 222 and barrels 235, 243 such that each axis 226 is not perpendicular to crossbar 110. Furthermore, while FIG. 1 depicts each pivot axis 226 as having the same orientation with respect to the crossbar 110, in some embodiments, the hinges 220 may distinctly orient the pivot axes 226 with respect to the crossbar 110 so as to provide pivot axes 226 that are oriented differently from one another.

A proximal end 262 of each side-load connector 260 may be pivotably coupled to a distal end 244 of its respective distal arm portion 244 via a hinge 250. Each hinge 250 may be defined by one or more barrels 263 of the side-load connector 260, one or more barrels 245 of the distal arm portion 240, and a pin 252. The barrels 245 may interleave with the barrels 263 and define a longitudinal aperture 254. Each pin 252 may pass through the aperture 254 defined by barrels 245, 263, thereby pivotally coupling distal ends 244 of the distal arm portions 240 to respective proximal ends 262 of the side-load connectors 260.

Each hinge 250 may provide a pivot axis 256 about which the side-load connector 260 may pivot. As shown, the hinges 250 may provide pivot axes 256 that are coplanar with and parallel to crossbar 110 and pivot axes 216. In other embodiments, the hinges 250 may orient pins 252, barrels 245, and barrels 263 such that each axis 256 is not coplanar with and/or is not parallel to cross bar 110 and/or pivot axes 216. Furthermore, while each pivot axis 256 is depicted as having the same orientation with respect to the crossbar 110, in some embodiments, the hinges 250 may distinctly orient the pivot axis 256 with respect to the crossbar 110 so as to provide pivot axes 256 that are oriented differently from one another.

The side-load connector 260 may include a port 264 that passes through the a distal portion 266 of the side-load connector 260. In particular, the port 264 may extend between an upper surface 265 and a lower surface 266 of the side-load connector 260. The side-load connector 260 may further include an opening 268 in a sidewall 270 of the connector 260. The opening 268 is configured to receive a longitudinal side of an attachment post 330 of the retractor blade 300 and permit the port 264 to receive the attachment post 330 as the attachment post 330 passes through the sidewall opening 268. Accordingly, the side-load connector 260 permits a lateral coupling of a retractor blade 300 to the an arm 200. Such a lateral coupling may be more convenient for the practitioner than a vertical coupling via the upper or lower surfaces 265, 266 of the connector 260, especially when the retractor blade 300 is positioned in a patient prior to attachment to the arm 200. Moreover, such a vertical coupling would not be possible while the handle assembly 400 is attached to the retractor blade 300 since the handle assembly 400 is too large to pass through the port 264. Further details concerning various embodiments of a side-load connector are presented below.

Finally, an angle adjustment assembly 280 may engage the proximal arm portion 230 and the distal arm portion 240 and adjust a relative angle between the proximal arm portion 230 and the distal arm portion 240. In particular, the angle adjustment assembly 280 may comprise a thumb screw 282 having a handle 284 at a proximal end of a threaded shaft 286 and a ball 288 at a distal end of the thread shaft 286. As shown in FIG. 1C, the shaft 286 may pass through a threaded aperture 237 of the proximal arm portion 230. Moreover, the ball 288 may be received by a socket 249 of the distal arm portion 240. Due to threads of the shaft 286 engaging threads of the aperture 237, rotation of the handle 284 thumb screw 282 to either extend or retract the ball 288 with respect to the threaded aperture 237.

With reference to FIG. 1B, extension of the ball 288 causes the distal arm portion 240 to rotate about the axis 226 in a clockwise direction. Conversely, retraction of the ball 288 causes the distal arm portion 240 to rotate about the axis 226 in a counter-clockwise direction. Thus, via the rotation of the thumb screw 284, the practitioner may adjust the angle of the distal arm portion 240 with respect to the proximal arm portion 230. Such adjustment may in turn adjust the angle of the retractor blades 300 shown in FIG. 1A. In reference to FIG. 1A, extending the ball 288 may cause the distal ends of the blades 200 to angle away from each other whereas retracting the ball 288 may cause the distal ends to angle toward each other.

Other embodiments of the self-retaining retractor 100 may include alternative retractor arms 200. For example, an alternative self-retaining retractor 100 may replace one of the distractor arms 200 with a stationary arm that is coupled to the crossbar 110 in a manner that prevents travel of the arm along the crossbar 110. Other embodiments of the self-retaining retractor 100 may include fewer or additional arms 200. For example, an alternative retractor 100 may include three arms 200 or only one arm 200. Various alternative embodiments may utilize fewer arm portions or more arm portions than the two arm portions of retractor arms 200. For example, a retractor arm may include only single arm portion and no hinges.

Figure 2B:
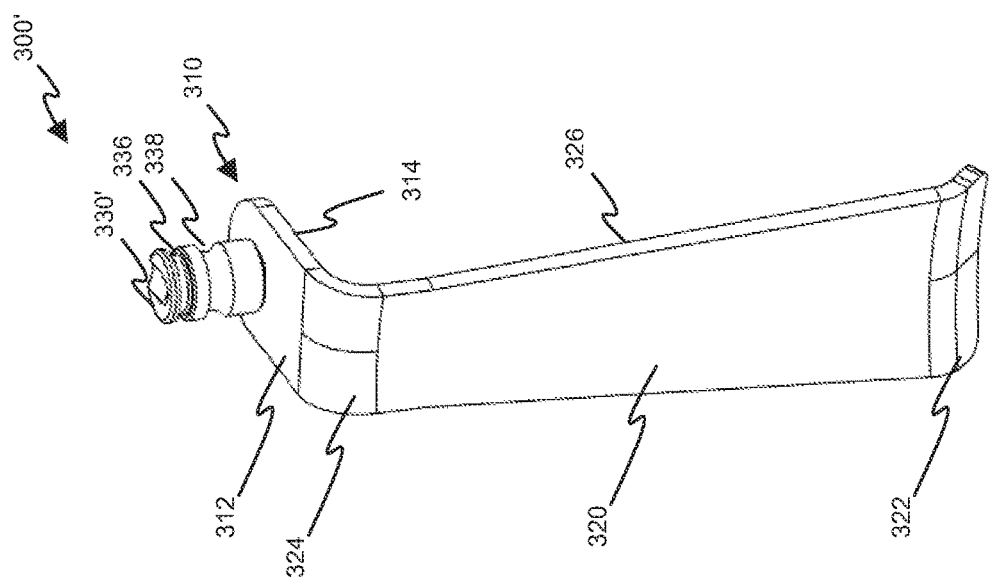
FIG. 2A-2B depict retractor blades of the retractor system of FIGS. 1A-1C.
Figure 2A:
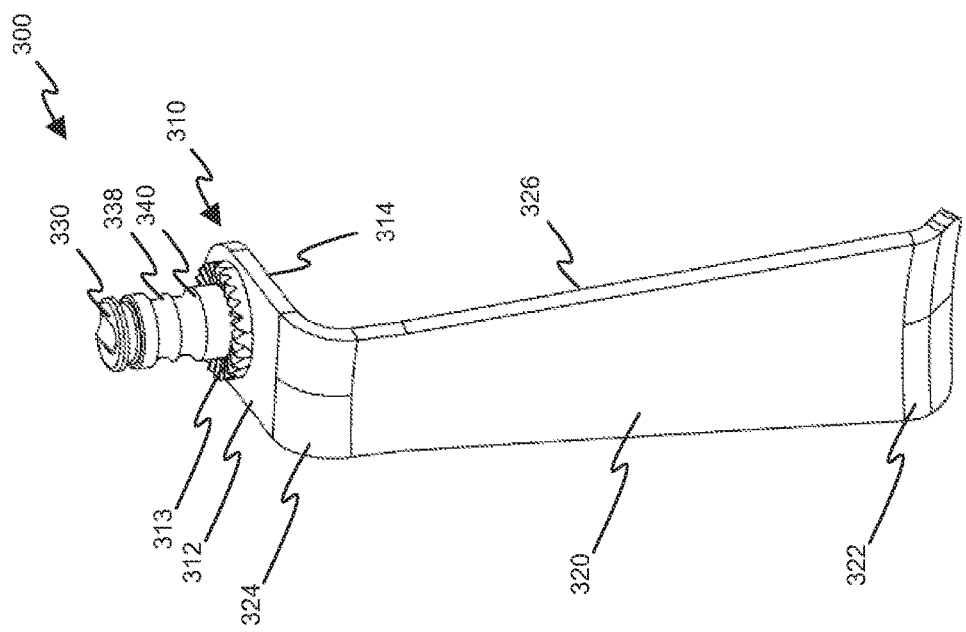

Referring now to FIGS. 2A and 2B, a perspective view of a first retractor blade 300 and a second retractor blade 300' in accordance with various aspects of the present disclosure are presented. In general, each retractor blade 300, 300' comprises a retractor body 310 and one or more blades 320 extending therefrom. Each blade 320 may comprise a smooth, thin plate with dull edges that is inserted into an incision to pull back the tissue. The blades 320 may come in many different sizes depending on the particular application and physical characteristics of the patient. The blades 320 may be slightly curved or completely flat, and may have end prongs of various configurations to make it easier to pull back tissue.

As depicted, the a blade 320 may comprise a distal end 322, a proximal end 324, a retracting portion 326. The distal end 322 generally corresponds to the end of the blade 320 inserted into an incision of a patient during a surgical procedure, and the proximal end 324 generally corresponds to the end of the blade 310 extending from the incision and out of the patient during a surgical procedure.

The proximal end 324 adjoins the retractor body 310, resulting in the retracting portion 326 generally extending or projecting from the retractor body 310 toward the distal end 322. As shown, the retracting portion 326 may form a 90° angle with the retractor body 310; however, other angles between the retracting portion 326 and the retractor body 310 are contemplated and may be more suitable for certain surgical procedures. The retracting portion 326 may be sized and adapted to hold back tissue from a site of interest during a procedure. In certain embodiments, the retractor system 10 may include a number of differently sized and/or shaped blades 320 to provide increased adaptability for different procedures and/or patients.

As noted above, the retractor body 310 is attached to one or more blades 320. As shown, the retractor body 310 may comprise a generally planar upper surface 312 and a generally planer lower surface 314 that is coplanar with the upper surface 312. The retractor body 310 may further include an attachment post 330, 330'. The attachment post 330 is shown in greater detail in FIG. 3. In particular, the attachment post 330, 330' may extend upwardly from the upper surface 312 of the retractor body 310, whereas the blade may extend downwardly from the upper surface 312 of the retractor body 310.

The attachment post 330, 330' may be sized and adapted for attachment to the side-load connector 260 of the retractor arm 200. To this end, the attachment post 330, 330' may have a generally cylindrical-shape with a circular cross-section. The attachment post 330 may extend from the upper surface 312 of the retractor body 310. In one embodiment, a longitudinal axis AA of the attachment post 330, 330' extends at a right angle from the upper surface 312; however, the attachment post 330 in some embodiments may extend from the upper surface 312 at other angles.

Figure 3:
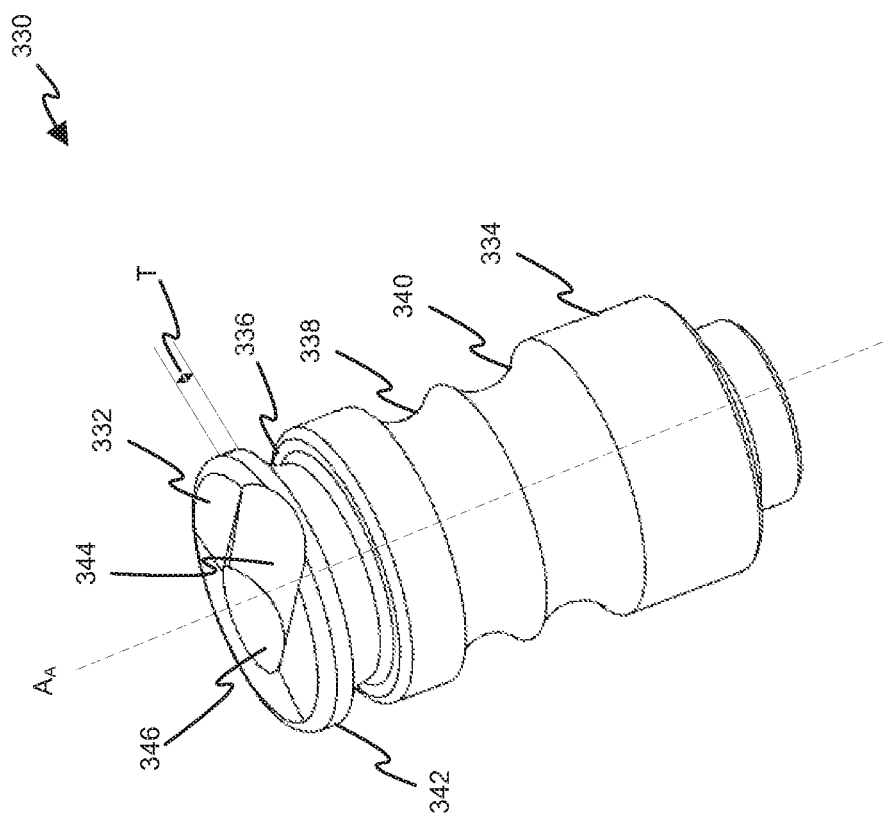
FIG. 3 provides a detailed, perspective view for an attachment post of the retractor blade shown in FIG. 2A.

As labeled in FIG. 3, the attachment post 330 may include a top surface 332 and a side surface 334. The side surface 334 may include upper, central, and lower groove 336, 338, 340. Each of the grooves 336, 338, 340 may be circumferential around the attachment post 330. The diameter of the attachment post 330 may be sized such that the attachment post 310 may pass through the side opening 268 to an attachment port 264 of the side-load connector 260.

The central groove 338 and the lower groove 340 may be positioned along the side surface 334 to vertically align the attachment post 330 within the port 264. As explained below, a cam or other member of a side-load connector may engage either the central groove 338 or the lower groove 340 to position the attachment post 330 longitudinally within the port 264. The side surface 334 and grooves 338, 340 may be tapered. Such tapering may aid or guide a cam or other member of the side-load connector into engagement with the grooves 338, 340, thus helping to longitudinally align the attachment post 330 within the port 264.

As shown in FIG. 2A, the lower groove 340 is longitudinally displaced along the side surface 334 closer to the retractor body 310 than the central groove 338 is to the retractor body 310. Moreover, the upper surface 312 of the retractor body 320 may include a serrated surface or teeth 313. Similarly, the lower surface 266 of the side-load connector 260 may include a serrated surface or teeth 269. See, e.g., FIGS. 1B and 1C. In one embodiment, the lower groove 340 is positioned along the side surface 334 such that the teeth 269 engage the teeth 313 and restrict rotation of the attachment post 330 when the lower groove 340 is engaged by the side-load connector 260.

The central groove 338 provides an attachment location that results in the upper surface 312 of the retractor body 310 being offset from a lower surface 266 of the side-load connector 260. In particular, the central groove 338 may be longitudinally displaced along the side surface 334 such that, when engaged by the side-load connector 260, the teeth 269 of the side-load connector 260 are positioned away from and not engaged with the teeth 313 of the retractor body 310. See, FIG. 1C. By engaging the grooves 338, 340, the side-load connector 260 may prevent the attachment post 330 from longitudinally traversing the port 264. However, due to the central groove 338 being circumferential around the side surface 334 and the teeth 269, 313 being disengaged, the attachment post 330 may freely rotate about the longitudinal axis AA. Thus, by aligning the attachment post 330 per the central groove 338 or the lower groove 340, a practitioner may selectively choose between (i) allowing the retractor blade 300 to freely rotate or swivel about the axis Aa, or (ii) locking the retractor blade 300 to the connector 260 and thereby preventing the retractor blade 300 from freely rotating or swiveling about the axis Aa.

Finally, the upper groove 336 may define a flange 342 to which a manipulator or handle may be attached. In one embodiment, the upper groove 336 is too small to receive a cam or other member of the side-load connector 260, thus reducing the chance of accidental, vertical misalignment of the attachment post 330 within the port 262.

FIG. 3 depicts the attachment post 300 with three grooves 336, 338, 340. However, the attachment post 300' of FIG. 2B includes only grooves 336, 338. The attachment post 300' is suitable for embodiments that are not concerned with providing a selective swivel lock feature. For example, as shown in FIG. 2B, the retractor blade 300' may lack the serrated surface 313 of FIG. 2A. Thus, the retractor blade 300' may be used in procedures where locking or preventing swiveling of the retractor blade 300' is not warranted or is undesirable. It should be appreciated, that the post 330' may also be used with retractor blades having the serrated surface 313 of FIG. 2A. Such a retractor blade would lock or prevent swiveling of the retractor blade 300' when used with a side-load connector 260 having teeth 269.

Figure 4B:
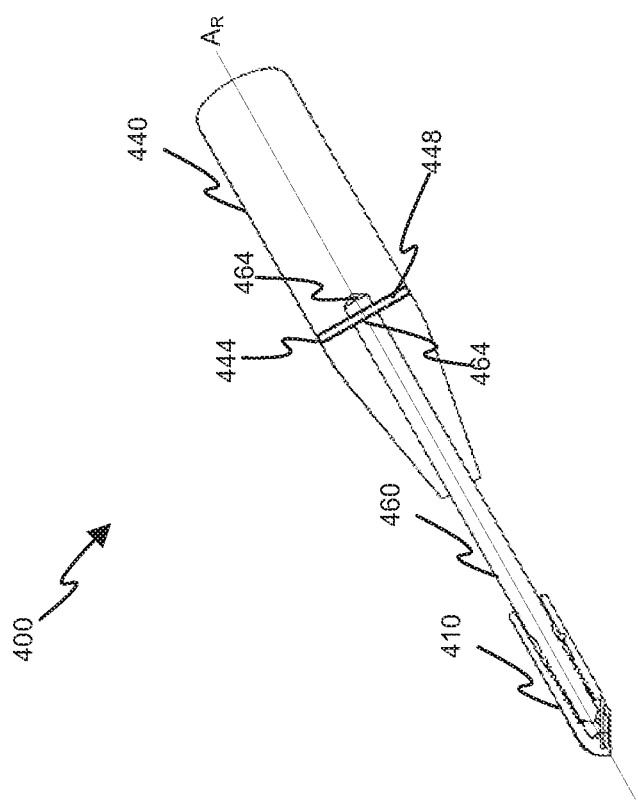
FIG. 4A-4C depict a handle assembly suitable for use with the retractor blades of FIGS. 2A-2B.
Figure 4A:
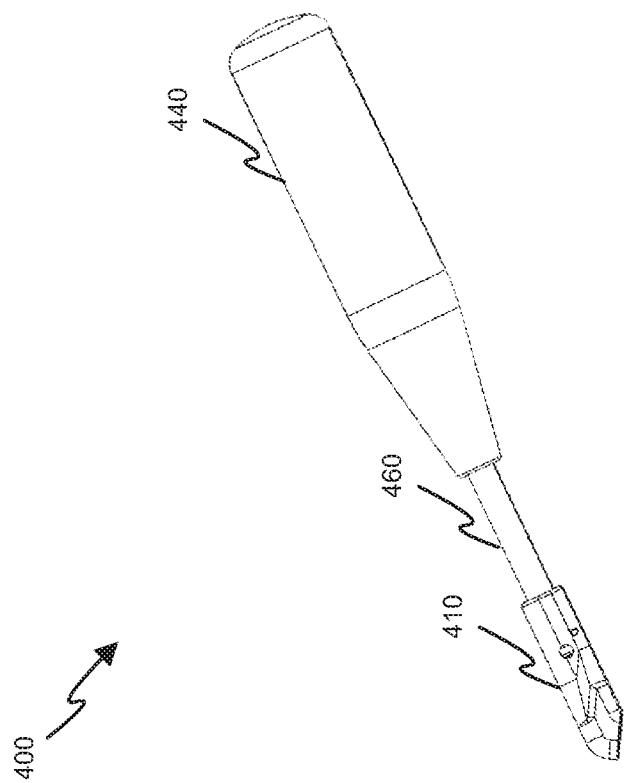
Figure 4C:
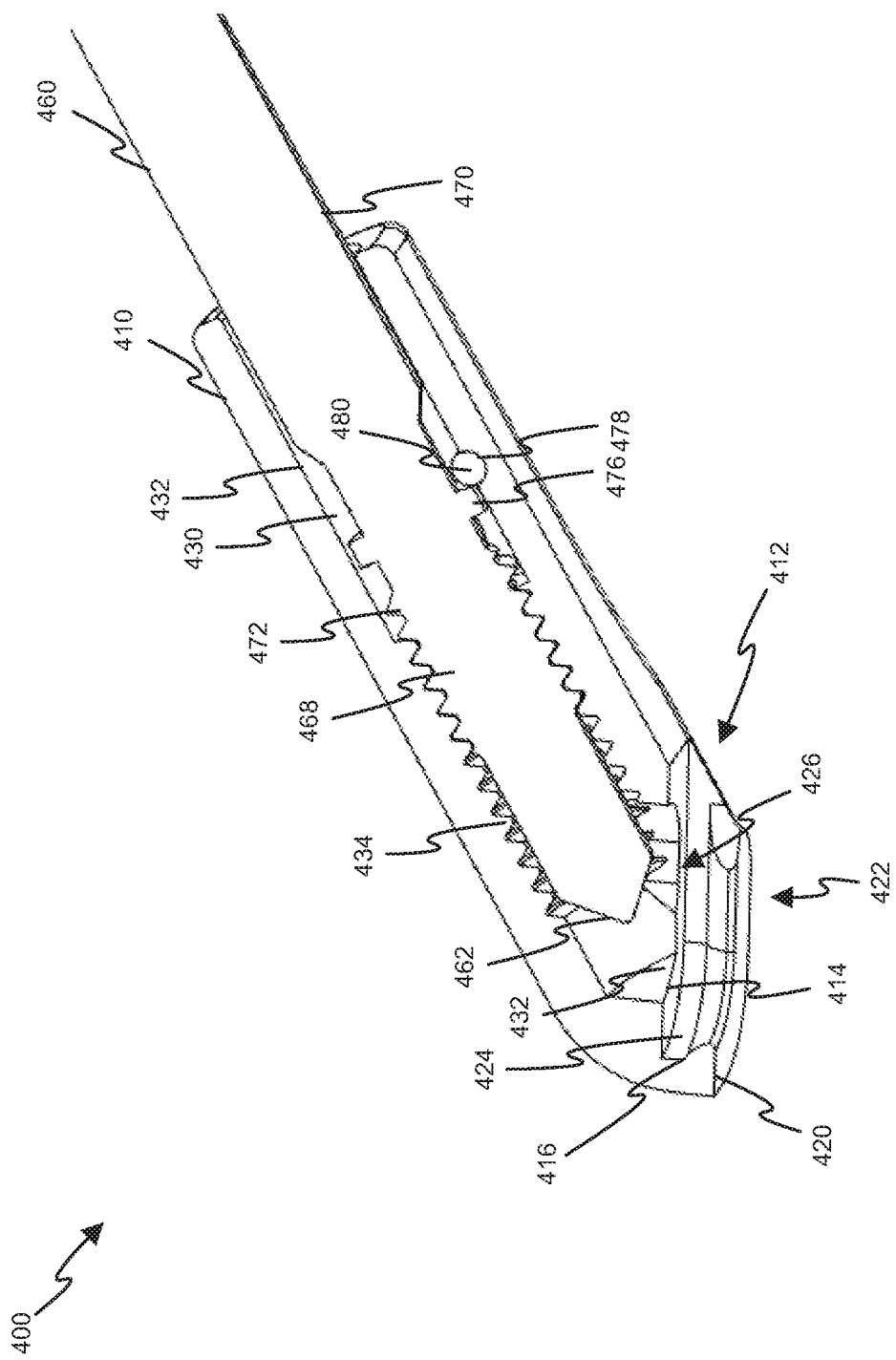

A practitioner may attach a handle assembly to the attachment post 330 to position the retractor blade 300 during a procedure. FIGS. 4A-C depict a handle assembly 400 suitable for attaching to the attachment post 330 via flange 342. In particular, the handle assembly 400 may be attached to the retractor blade 300 via a slidable engagement with the flange 342. To this end, the handle assembly 400 may include an attachment portion 410, a handle 440, and a retaining rod 460. The retaining rod 460 may secure the handle 440 to the attachment portion 410. Moreover, the retaining rod 460 may be manipulated to selectably engage a recess 344 in the top surface 332 of the attachment post 330.

The attachment portion 410 may be sized and adapted to cooperate with the attachment post 330. As shown in FIG. 4C, the attachment portion 410 may comprise a slot 412 that is sized and adapted to accept and mate with flange 342 of the attachment post 330. The slot 412 may comprise an upper surface 414 and a lower surface 416. The lower surface 416 may be spaced apart from the upper surface 414 by a distance slightly larger than a thickness T of the flange 342. In this manner, the attachment post 330 may be received by the slot 412 such that surfaces 414, 416 of the slot 412 closely mate and engage surfaces of the flange 342.

Furthermore, a lower surface 420 of the slot 412 may include an opening 422 sized to receive and closely mate with the attachment post 330. The slot 412 may further comprise an end wall 424. The end wall 424 may be sized to receive and closely mate with the flange 342 of the attachment post 330. In particular, the end wall 424 and upper groove 336 may cooperate to properly position the attachment post 330 within the slot 412. In particular, the end wall 424 may stop further advancement of the attachment post 330 into the slot 412.

Finally, the upper surface 414 of the slot 412 includes an aperture 426. In particular, the aperture 426 is positioned in the upper surface 414 such that the aperture 426 aligns with the recess 344 in the attachment post 330. The aperture 426 is sized to closely mate with a tip 462 of the retaining rod 460. As shown, the tip 462 may be beveled or tapered. Such tapering may help guide the tip 462 into the recess 344 even in the presence of minor misalignment of the recess 344 with the aperture 426. For example, a practitioner may fail to fully insert the attachment post 330 into the slot 412. The tapered tip 462 may aid the retaining rod 460 in sliding into the recess 344 and urging the attachment post 330 into a fully inserted position.

Referring to FIG. 4B, the handle 440 may be sized and adapted to be grasped by a practitioner. The handle 440 may include an aperture 442 sized to receive a proximal end 464 of the retaining rod 460. The handle 440 may further include an aperture 444 which may be aligned with a corresponding aperture 466 toward the proximal end 464 of the retaining rod 460. A pin 448 may be passed through the apertures 442, 466 thereby securing the handle 440 to the retaining rod 460. As such, a practitioner may rotate the handle 440 about the longitudinal axis $A_R$ of the rod 460 in order to rotated and advance the retaining rod 460.

The attachment portion 410 may include a longitudinal cavity 430 that is sized and adapted to receive a threaded end 468 of the retaining rod 460. As shown, a distal end 432 of the longitudinal cavity 430 may adjoin the aperture 426. The cavity 430 may be shaped and sized such that its inner walls 432 closely mate with side walls 470 of the retaining rod 460 and permit the retaining rod 460 to slide longitudinally along at least a portion of the cavity 430. The inner walls 432 may include threads 434 toward the distal end 432. The threads 434 are configured to engage threads 472 of the retention rod 460.

As a result of such threads 434, 472, the retaining rod 460 may be advanced through the cavity 430 via rotation of the handle 440 in a first direction about the longitudinal axis $A_R$. Conversely, rotation of the handle 440 in a second direction opposite the first direction may withdrawal the retaining rod 460 from the cavity 430. As the retaining rod 460 advances into the cavity 430, the tip 462 of the retaining rod 460 may engage the recess 344 of the attachment post 330. Further advancement of the retaining rod 460 may advance the tip 462 toward a distal end 346 of the recess 344 until the tip 462 engages the distal end 346. By engaging the distal end 346, the retaining rod 460 prevents withdrawal of the flange 342 from the attachment portion 410. Once engaged, an annular rib 476 of retaining rod 460 clears an aperture 478 in the attachment portion 410. A pin 480 may then be inserted into the aperture 478. The pin 480 may engage and block the passage of the annular rib 476, thereby preventing withdrawal of the retaining rod 460 from the attachment portion 410. In this manner, the retaining rod 460 may be secured to the attachment portion 410, thus preventing detachment of the handle assembly 400 from the retractor blade 300.

Once the handle assembly 440 is secured to the retractor blade 300, the handle 440 provides for convenient manipulation and placement of the retractor blade 330. Once the retractor blade 330 is positioned as desired, the practitioner may attach the blade 300 to the side-connector 260 via the sidewall opening 268. After attaching the retractor blade 300, the practitioner may remove the pin 480 from the attachment portion 410. The practitioner may then rotate the handle 440 about longitudinal axis $A_R$ to withdrawal the retaining rod 460 from the attachment portion 410 and disengage the retaining rod 460 from the attachment post 330. After such disengagement, the handle assembly 440 may be detached from the retractor blade 330.

To use the retractor system 10, the self-retaining retractor 100 may be first secured to a frame assembly of a surgical table via the attachment post 116. With the patient in place, an incision is made to provide access to the operative site of interest. Retractor blades 300 are then selected and secured to handle assemblies 400. The retractor blades 300 are then inserted, distal end 322 first, into the operative site of interest, and positioned as desired via handle assemblies 400 to retract tissue and provide access to the surgical site of interest. Once positioned as desired, the retractor blades 300 may be secured to the retractor 100 via side-load connectors 260. Again, the practitioner may use the handle assemblies 400 to aid in aligning and connecting the retractor blades 300 with the side-load connectors 260. Thus, the retractor blades 300 are secured at both distal and proximal ends, removing the need for manual holding of the retractor blades 300 during the procedure. As such, the practitioner may remove the handle assemblies 400 after securing to the side-load connectors 260 in order to provide better access to the surgical site.

Figure 5A:
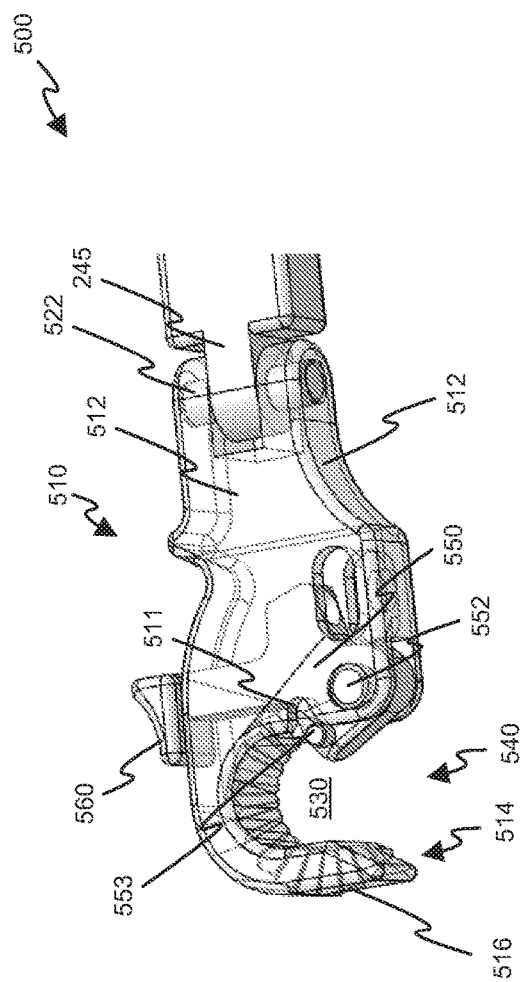
FIGS. 5A-5B depict a first embodiment for a side-load connector of the retractor system of FIGS. 1A-1C.
Figure 5B:
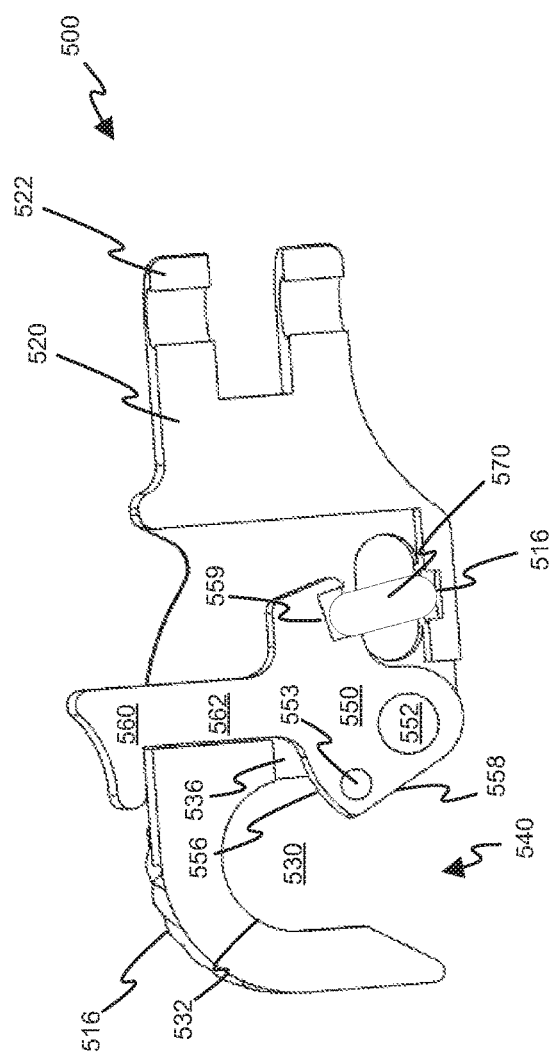

Referring now to FIGS. 5A and 5B, one embodiment of a side-load connector suitable for implementing the side-load connector 260 of FIGS. 1A-1C is shown. The side-load connector 500 of FIGS. 5A and 5B may include a housing 510 having an upper surface 512, a lower surface 514 with a serrated portion or teeth 516, and a side surface or sidewall 518 adjoining the upper surface 512 and the lower surface 514. A proximal end 520 of the side-load connector 500 may include one or more barrels 522 which may interleave with one or more barrels 245 of the distal arm portion 240 (see, FIGS. 1A-1C) to form a hinge in a manner similar to the hinge 250 discussed above in regarding to FIGS. 1A-1C.

As shown, the side-load connector 500 further includes a port 530, an sidewall opening 540, a cam 550, a button 560, and a spring 570. The port 530 provides a cylindrical aperture that passes through the upper surface 512 and lower surface 514. While the port 530 is generally cylindrical, the sidewall opening 540 passes through the sidewall 518 of the housing 510 to the port 530. As such, an inner wall 532 of the port 530 is broken by the sidewall opening 540. Due to such discontinuity in the inner wall 532, the inner wall 532 only partially circumscribes the port 530, thus permitting loading the attachment post 330 via the sidewall opening 540. Moreover, the port 530 has a diameter that is slightly larger than the diameter of the attachment post 330. As such, the inner wall 532 may closely mate with the longitudinal sidewall 334 of the attachment post 330 when the attachment post 330 is loaded into the port 530.

As shown, the cam 550 is pivotably coupled between the upper surface 512 and the lower surface 514 via a pin 552 positioned adjacent the sidewall opening 540. The pin 552 permits the cam 550 to rotate about a pivot point between an open position (not shown) and closed position depicted in FIGS. 5A and 5B. When in the closed position, the cam 550 includes a first distal portion 556 and a second distal portion 558 that extends radially from the pin 552 and into the sidewall opening 540.

From the closed position of FIGS. 5A and 5B, the button 560 may be slid toward the proximal end 520 of the side-load connector 500 to rotate the cam 550 to the opened position. As shown, the button 560 is coupled to the cam 550 via a lever 562. Sliding the button 560 toward the proximal portion 540 thus causes the first and second distal portions 556, 558 to rotate inwardly toward the port 530. The first distal portion 556 provides circular surface with respect to the pivot point provided by the pin 552. As such, while the cam 550 rotates inwardly toward the port 530 when transitioning toward the opened position, the first distal portion 556 generally maintains the distance between itself and the opposite inner wall 532 of the port 530. As such, the cam 550 may remain engaged with a groove 338, 340 of the loaded attachment post 330 as the cam 550 slides past the loaded post 330 and into a recess 536 in the inner wall 532.

Furthermore, the cam 550 may include a stop 553 that extends from the cam 550 as shown in FIG. 5A. The housing 510 may include a recess 511 configured to receive the stop 553 as the cam 550 rotates toward the opened position. Moreover, an end of the recess is positioned to engage the stop 553 and prevent further rotation of the cam 550 when the cam 550 fully reaches the opened position. In this manner, the stop 553 and the recess 511 may prevent the button 560 from rotating the cam 550 past the opened position.

As noted above, the cam 550 further includes the second distal portion 558. Unlike the first distal portion 556 which provides circular surface, the second distal portion 558 extends linearly from the pin 552. Due to such the linear nature of the second outer edge portion 558, as the cam 550 rotates toward the opened position, the second distal portion 558 retracts from the sidewall opening 540 to permit passage of the attachment post 330 into and/or out of the port 530 via the sidewall opening 540.

The spring 570 may be positioned between the sidewall 516 and a seat 559 in the cam 550. Due to such positioning, the spring 570 may apply a biasing force to the cam 500 that biases the cam 550 toward the closed position. Accordingly, when no external forces are applied to the cam 550, the spring 570 places the cam 550 in the closed position.

When side loading the attachment post 330, the practitioner may press the attachment post 330 against the second distal portion 558, which provides a tapered opening toward the port 530. As the attachment post 300 continues to travel toward the port 530, the attachment post 300 overcomes the biasing force of the spring 570, thus causing the cam 550 to rotated toward the opened position. When the attachment post 300 is loaded into the port 530, the attachment post 300 is positioned beyond the second distal portion 558 and comes in contact with the first distal portion 556. Due to the first distal portion 556 maintaining a distance to the opposite inner wall of the port 530 that is slightly large that the diameter of the grooves 338, 340, the spring 570 causes the cam 550 to snap back to the closed position once the attachment post 330 is loaded and one of the grooves 338, 340 is aligned with the cam 550.

To unload retractor blade 300, the practitioner may slide the button 560 toward the proximal end 520 of the connector 500 to place the cam 550 in the opened position. Once in the opened position, the practitioner may slide the attachment post 330 through the sidewall opening 540, thereby unloading or detaching the retractor blade 300 from the connector 500.

Referring now to FIGS. 6A and 6B, another embodiment of a side-load connector suitable for implementing the side-load connector 260 of FIGS. 1A-1C is shown. The side-load connector 600 of FIGS. 6A and 6B may include a housing 610 having an upper surface 612, a lower surface 614 with a serrated portion or teeth 616, and a side surface or sidewall 618 adjoining the upper surface 612 and the lower surface 614. A proximal end 620 of the side-load connector 600 may include one or more barrels 622 which may interleave with one or more barrels 245 of the distal arm portion 240 (see, FIGS. 1A-1C) to form a hinge in a manner similar to the hinge 250 discussed above in regarding to FIGS. 1A-1C.

As shown, the side-load connector 600 further includes a port 630, an sidewall opening 640, a cam 650, a button 660, and a spring 670. The port 630 provides a cylindrical aperture that passes through the upper surface 612 and lower surface 614. While the port 630 is generally cylindrical, the sidewall opening 640 passes through the sidewall 618 of the housing 610 to the port 630. As such, an inner wall 632 of the port 630 is broken by the sidewall opening 640. Due to such discontinuity in the inner wall 632, the inner wall 632 only partially circumscribes the port 630, thus permitting loading the attachment post 330 via the sidewall opening 640. Moreover, the port 630 has a diameter that is slightly larger than the diameter of the attachment post 330. As such, the inner wall 632 may closely mate with the longitudinal sidewall 334 of the attachment post 330 when the attachment post 330 is loaded into the port 630.

As shown, the cam 650 is pivotably coupled between the upper surface 612 and the lower surface 614 via a pin 652 positioned adjacent the sidewall opening 640. The pin 652 permits the cam 650 to rotate about a pivot point, between an opened position (not shown) and a closed position depicted in FIGS. 6A and 6B. When in the closed position, the cam 650 includes a first distal portion 656 and second distal portion 658 that extend radially from the pin 652 and into the sidewall opening 640.

From the closed position of FIGS. 6A and 6B, the button 660 may be pressed into the housing 610 to cause the button 660 to engage and rotate the cam 650 to the opened position. As shown, the button 660 comprises a distal end 662 that extends into the housing 610 and is coupled to the cam 550 at a pivot point 664. Pressing the button 660 forces the distal end 662 downward, causing the cam 650 to rotate the first distal portion 656 of the cam 650 inwardly toward the port 630. The first distal portion 656 provides circular surface with respect to the pivot axis of the pin 652. As such, while the cam 650 rotates inwardly toward the port 630 when transitioning toward the opened position, the first distal portion 656 generally maintains the same distance between itself and the opposite inner wall 632 of the port 630. As such, the cam 650 may remain engaged with a groove 338, 340 of the loaded attachment post 330 as the cam 650 slides past the loaded post 330 and into a recess 636 in the inner wall 632.

Furthermore, the button 660 may include a stop or lip 666 positioned between a proximal end 668 of the button 660 and its distal end 662. In particular, the stop 666 is positioned to engage an outer edge 659 of the cam 650 when the cam 650 fully reaches the opened position. In particular, the stop 666 prevents further inward movement of the button 660 when it engages the cam 650. Since inward movement of the button 660 is prevented, further rotation of the cam 650 to which the button 660 is coupled is prevented. In this manner the stop 666 may prevent the button 660 from rotating the cam 650 past the opened position.

As noted above, the cam 650 further includes the second distal portion 658. Unlike the first distal portion 656 which provides circular surface, the second distal portion 658 provides a linear or radially decreasing surface from the pin 652. Due to such the radially decreasing nature of the second distal portion 658, as the cam 650 rotates toward the opened position, the second distal portion 658 retracts from the sidewall opening 640 to permit passage of the attachment post 330 into and/or out of the port 630 via the sidewall opening 640.

The torsion spring 670 may be coupled to a seat 617 in the housing 610 and to the cam 650 in order to provide a biasing force to the cam 650. In particular, the spring 670 may bias the cam 650 toward the closed position. Accordingly, when no external forces are applied to the cam 650, the spring 670 places the cam 650 in the closed position.

When side loading the attachment post 330, the practitioner may press the attachment post 330 against the second distal portion 658, which provides a tapered opening toward the port 630. As the attachment post 300 continues to travel toward the port 630, the attachment post 300 overcomes the biasing force of the spring 670, thus causing the cam 650 to rotate toward the opened position. When the attachment post 300 is loaded into the port 630, the attachment post 300 is positioned beyond the second distal portion 658 and comes in contact with the first distal portion 656. Due to the first distal portion 656 maintaining a distance to the opposite inner wall 632 of the port 630 that is slightly large that the diameter of the grooves 338, 340, the spring 670 causes the cam 640 to snap back to the closed position once the attachment post 330 is loaded and one of the grooves 338, 340 is aligned with the cam 640.

To unload retractor blade 300, the practitioner may press the button 660 into the housing 610 to place the cam 640 in the opened position. Once in the opened position, the practitioner may slide the attachment post 330 through the sidewall opening 640, thereby unloading or detaching the retractor blade 300 from the connector 600.

Figure 7A:
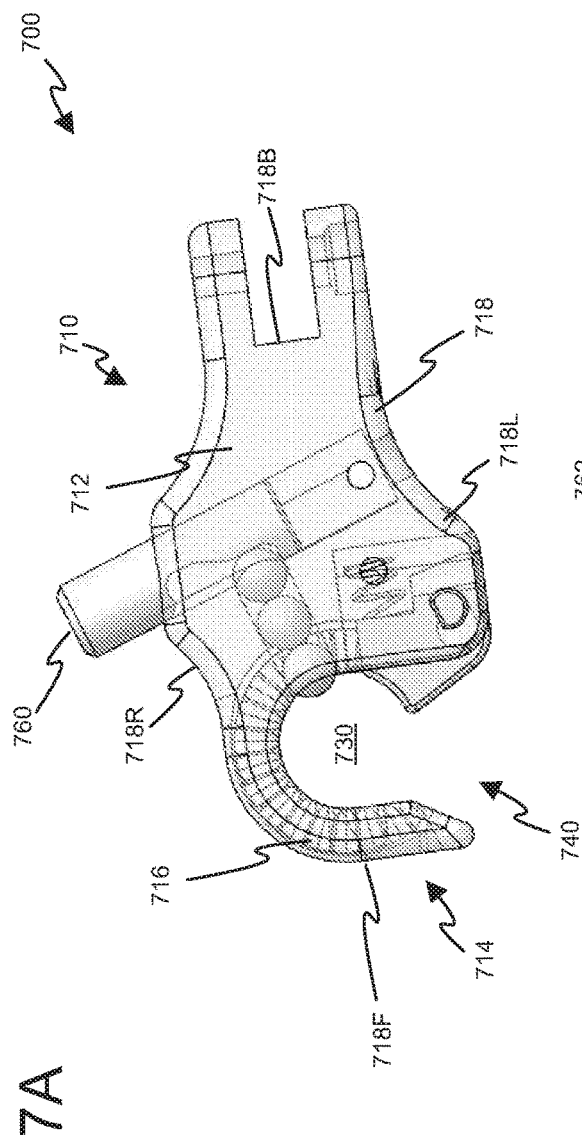
FIGS. 7A-7B depict a third embodiment for a side-load connectors of the retractor system of FIGS. 1A-1C.
Figure 7B:
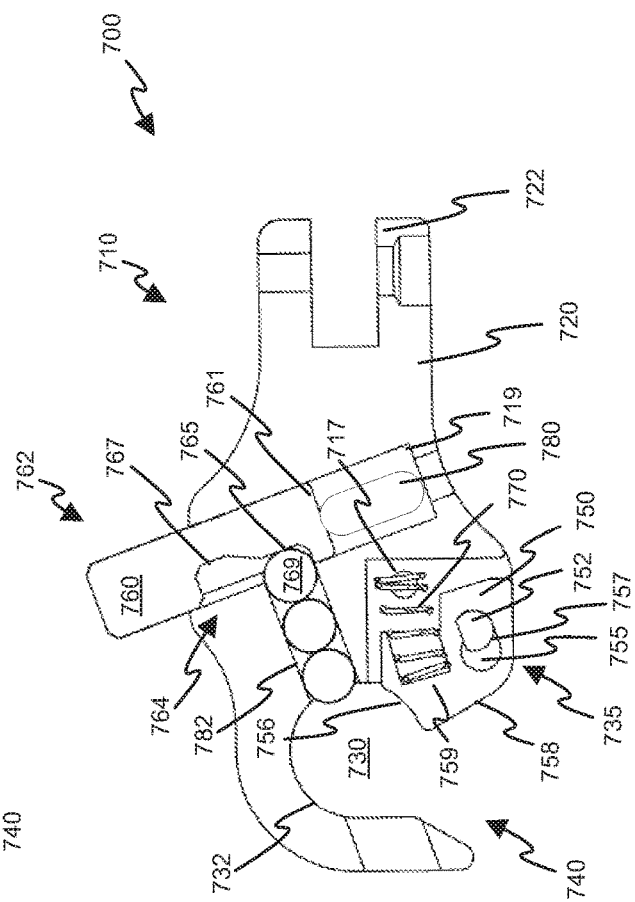

Referring now to FIGS. 7A and 7B, another embodiment of a side-load connector suitable for implementing the side-load connector 260 of FIGS. 1A-1C is shown. The side-load connector 700 of FIGS. 7A and 7B may include a housing 710 having an upper surface 712, a lower surface 714 with a serrated portion or teeth 716, and a side surface or sidewall 718 adjoining the upper surface 712 and the lower surface 714. A proximal end 720 of the side-load connector 700 may include one or more barrels 722 which may interleave with one or more barrels 245 of the distal arm portion 240 (see, FIGS. 1A-1C) to form a hinge in a manner similar to the hinge 250 discussed above in regarding to FIGS. 1A-1C.

As shown, the side-load connector 700 further includes a port 730, an sidewall opening 740, a cam 750, a button 760, a first spring 770, and a second spring 780. The port 730 provides a cylindrical aperture that passes through the upper surface 712 and lower surface 714. While the port 730 is generally cylindrical, the sidewall opening 740 passes through the sidewall 718 of the housing 710 to the port 730. As such, an inner wall 732 of the port 730 is broken by the sidewall opening 740. Due to such discontinuity in the inner wall 732, the inner wall 732 only partially circumscribes the port 730, thus permitting loading the attachment post 330 via the sidewall opening 740. Moreover, the port 730 has a diameter that is slightly larger than the diameter of the attachment post 330. As such, the inner wall 732 may closely mate with the longitudinal sidewall 334 of the attachment post 330 when the attachment post 330 is loaded into the port 730.

As shown, the cam 750 is pivotably coupled between the upper surface 712 and the lower surface 714 via a pin 752 positioned adjacent the sidewall opening 740. The pin 752 permits the cam 750 to rotate between an opened position (not depicted) and a closed position depicted in FIGS. 7A and 7B. When in the closed position, the cam 750 includes a first distal portion 756 and a second distal portion 758 that extends radially from the pin 752 and into the sidewall opening 740. The first distal portion 756 may generally engage a sidewall surface 332 of a loaded attachment post 330 when the cam 750 is in the closed position. The second distal portion 758 may generally provide an inwardly tapered surface when the cam 750 is in the closed position. Such tapering may aid a practitioner in loading an attachment post 330 of a retractor blade 330 into the port 730 as described below.

Unlike first distal portion of FIGS. 5A, 5B, 6A, 6B, the first distal portion 756 may provide a convex surface that is noncircular with respect to the pin 752. In particular, the curvature of the first distal portion 756 generally matches the radial curvature of the inner wall 732 of the port 730. As such, when in the closed position, the first distal portion 756 effectively extends the inner wall 732 and closely mates with the sidewall surface 334 of the attachment post 330. Moreover, in at least some embodiments, the first distal portion 756 does not engage grooves 338, 340 of a loaded attachment post 330 and thus further differs from first distal portions of FIGS. 5A, 5B, 6A, 6B.

When in the closed position, the cam 750 prevents a loaded attachment post 330 from being withdrawn from the port 730 via the sidewall opening 740. Unlike the embodiments of FIGS. 5A, 5B, 6A, and 6B, the button 760 does not engage or otherwise rotate the cam 750. As such, pressing the button 760 does not open the cam 750 to permit withdrawal of the loaded attachment post 330 via the sidewall opening 740. Instead, the cam 750 remains locked in the closed position, preventing such removal via the sidewall opening 740. To this end, the cam 750 includes a hole 753 for the pin 752 that includes a circular portion 755 and adjoining noncircular portion 757. As shown, the noncircular portion 757 is positioned more inwardly from the opening 740 than the noncircular portion 755. The pin 752 has a generally circular cross-section, but with a flattened side. When in the closed position, the pin 752 resides in the noncircular portion 757 of the hole 753 with its flattened side engaging a corresponding flat portion of the noncircular portion 757. In this manner, the pin 752 and noncircular portion 757 lock the cam 750 in place and prevent the loaded attachment post 330 from withdrawing via the sidewall opening 740.

Due to the shape of the hole 753, the cam 750 does not have a fixed pivot point about the pin 752. In particular, the pin 752 may transition between the circular portion 755 when in the opened state toward the noncircular portion 757 when in the closed state. In particular, the second distal portion 758 is effectively retracted from the port 730 as the cam 750 slides along the pin 752 toward the circular portion 755. Such retraction permits the cam 750 to slide past a loaded attachment post 330.

The first spring 770 may be coupled between a seat 717 in the housing 710 and a seat 759 in the cam 750 to provide a biasing force to the cam 750. In particular, the spring 770 may bias the cam 750 toward the closed position. Moreover, the first spring 770 may further bias the cam 750 away from the pin 752, thus causing the pin 752 to slide into the noncircular portion 757 of the hole 753 when in the closed position. Accordingly, when no external forces are applied to the cam 750, the spring 770 places the cam 750 in the closed position with the pin 752 in the noncircular portion 757 of the hole 753, thus locking the cam 750 in the closed position.

When side loading the attachment post 330, a practitioner may press the attachment post 330 against the second distal portion 758 of the cam 750, which provides a tapered opening toward the port 730. As the attachment post 300 continues to travel toward the port 730, the attachment post 300 overcomes the biasing force of the spring 770, thus causing the cam 750 to first slide inwardly such that the pin 752 traverses from the noncircular portion 757 to the circular portion 755 of the hole 753. With the pin 752 in the circularly portion 755, the cam 750 may rotate inward toward the opened position.

When the attachment post 300 is loaded into the port 730, the attachment post 300 is positioned beyond the second distal portion 758. Once the attachment post 300 is past the second distal portion 758, the spring 770 causes the cam 750 to snap back to the closed position. In particular, the biasing force first causes the cam 750 to rotate outwardly from the port 730 with the pin 752 in the circular portion 755 of the hole 753. Upon reaching or nearly reaching the closed position, the biasing force causes the pin 752 to slide into the noncircular portion 757 to lock the cam 750 in the closed position.

As explained above, the cam 750 does not engage the grooves 338, 340 of the loaded attachment post 330. Moreover, the button 760 does not engage or rotate the cam 750. Instead, the button 760 is part of a lock 762 which longitudinally locks a loaded attachment post 330 in the port 730. To this end, the button 760 includes a ramped recess 764. The ramped recess 764 is configured to receive a first bearing from one or more bearings 769 of the lock 762. In one embodiment, each bearing 769 comprises a spherical, ball bearing; however, bearings of other shapes may be used. As shown, the bearings 769 may reside in a channel 782 extending between the ramped recess 764 and the port 730. Moreover, the second spring 780 may reside between a seat 719 of the housing 710 and a lower surface 761 of the button 760. In this manner, the second spring 780 may bias the button outwardly from the housing 710 away from a released position toward a locked position.

In the locked position, a shallower portion 765 of the ramped recess 764 aligns with the channel 782. In the released position, a deeper portion 767 of the ramped recess 764 aligns with the channel 782. Thus, when in the locked position, the shallower portion 765 via the biasing force of the spring 780 urges the one or more bearings 769 toward the port 730, thereby causing the one or more bearings 769 to engage a groove 338, 340 of the loaded attachment post 300. In this manner, the engaged bearings 769 may longitudinally lock the loaded attachment post 330 within the port 730.

To unload retractor blade 300, the practitioner may press the button 760 into the housing 710 to place the ramped recess 762 into the released position. In the released position, the deeper portion 767 is aligned with the one or more bearings 769 thus removing the urging force of the spring 780. As such, the one or more bearings 769 may move away from the port 730 as the attachment post 330 longitudinally traverses the port 730. Thus, once the lock 762 is in the released position, the practitioner may withdrawal the attachment post 330 from the port 730 by pulling the attachment post 330 longitudinally away from the bottom surface 714 of the housing 710.

Figure 8A:
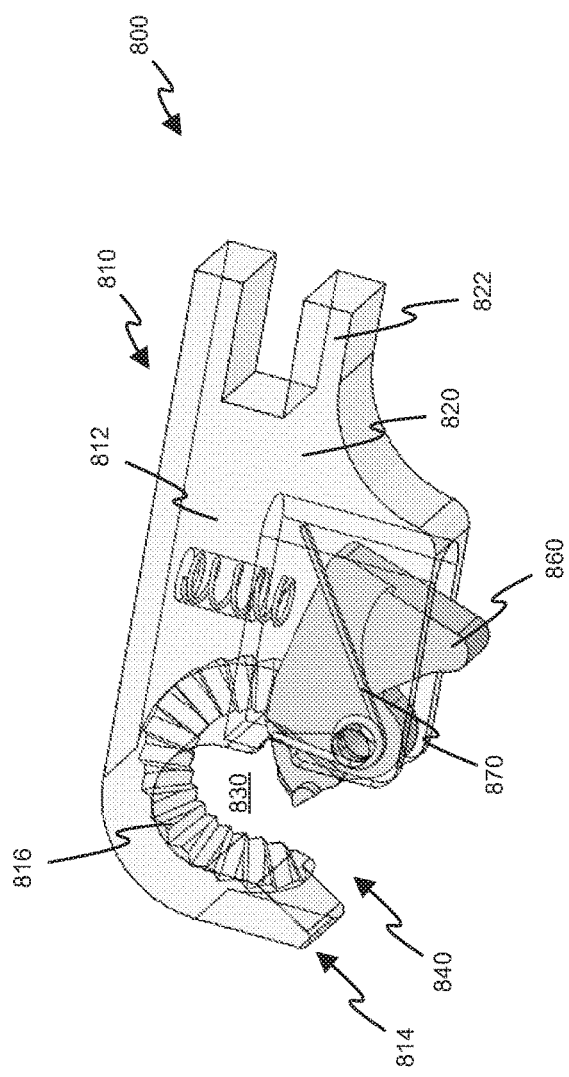
FIGS. 8A-8B depict a fourth embodiment for a side-load connector of the retractor system of FIGS. 1A-1C.
Figure 8B:
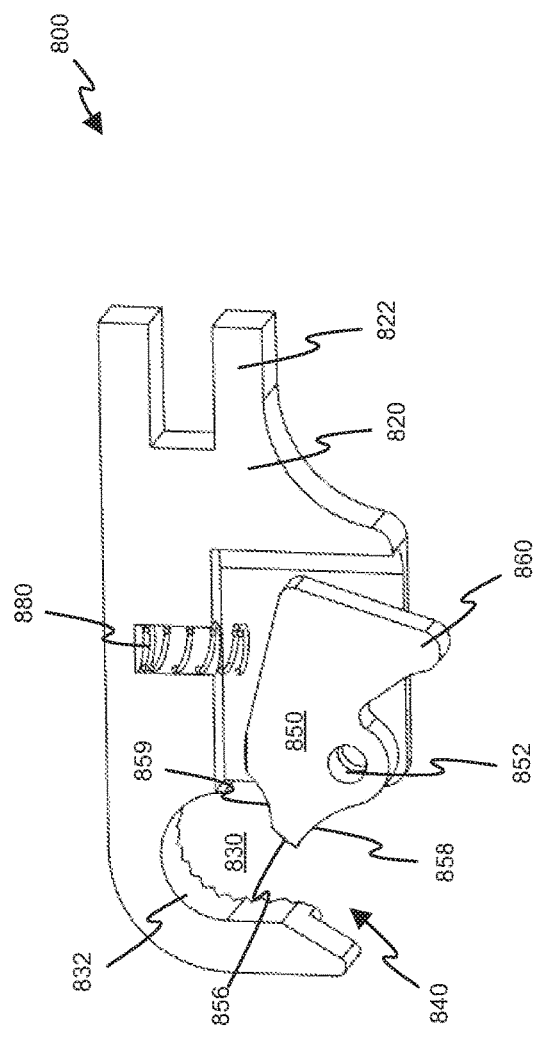
Figure 10A:
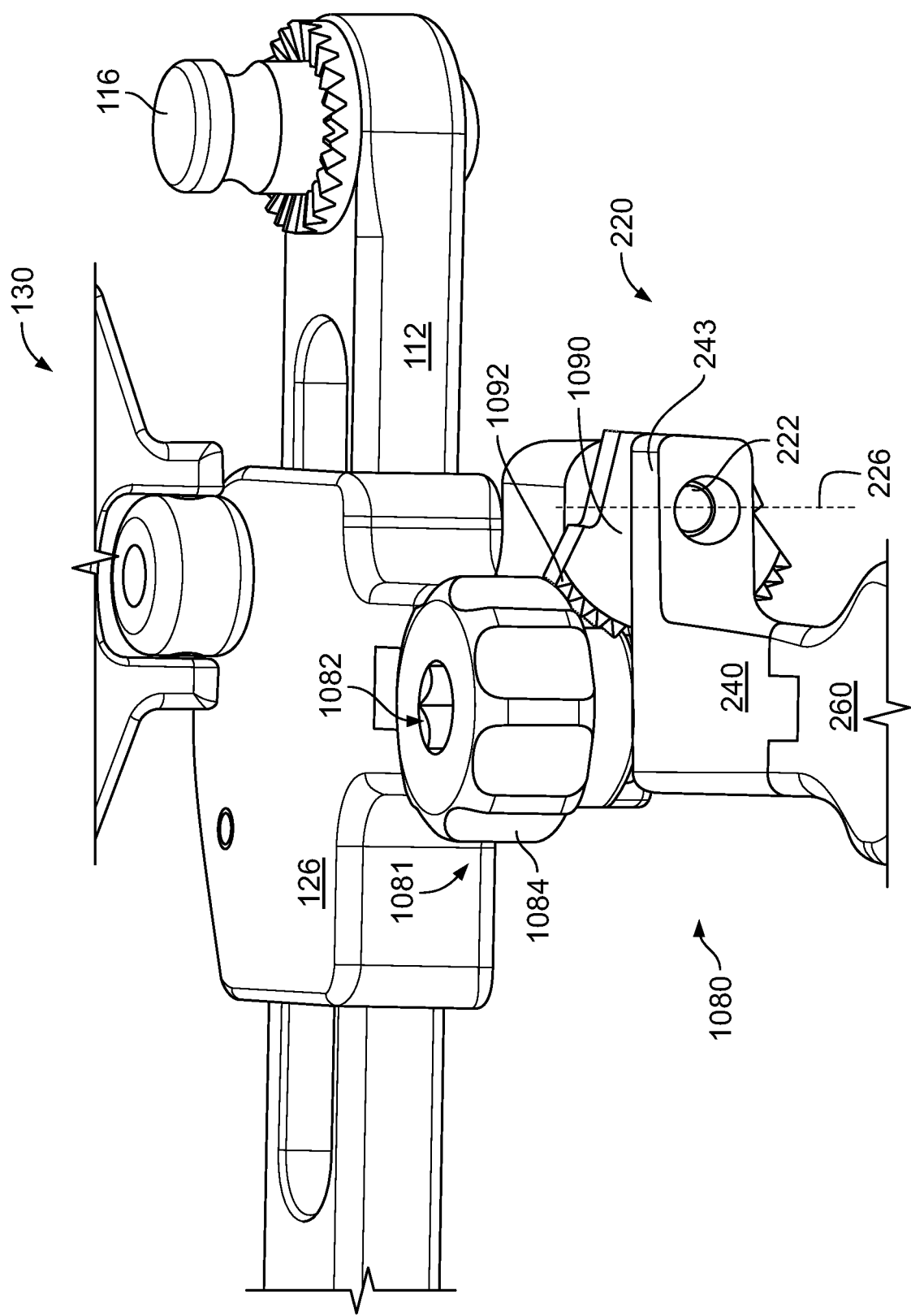
FIGS. 10A-10E depict another embodiment of a retractor arm for the retractor system of FIGS. 1A-1C that has an alternative embodiment of an angle adjustment assembly in accordance with various aspects of the present disclosure.
Figure 10B:
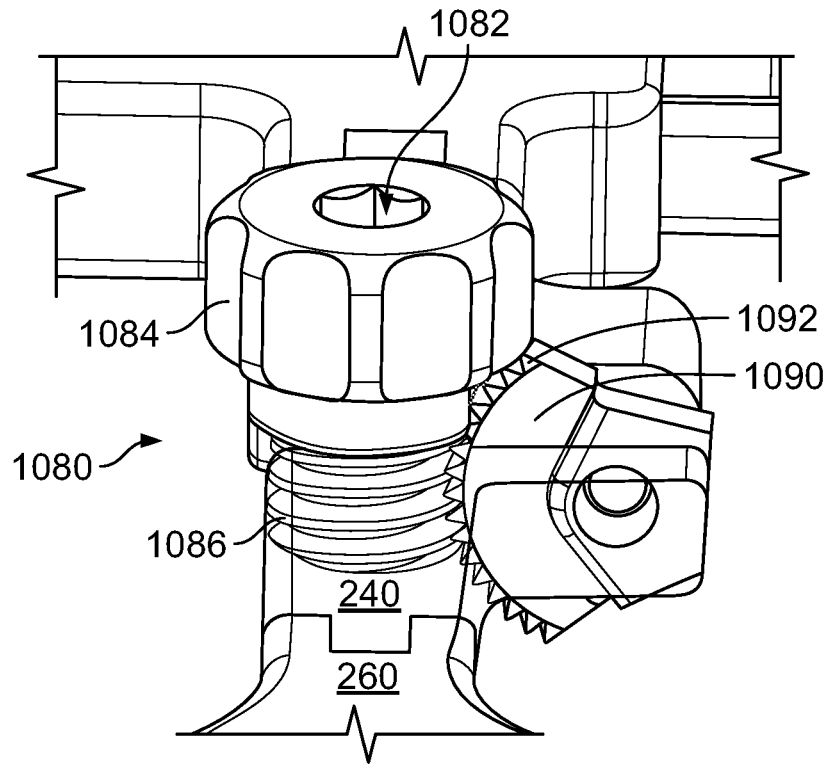
Figure 10C:
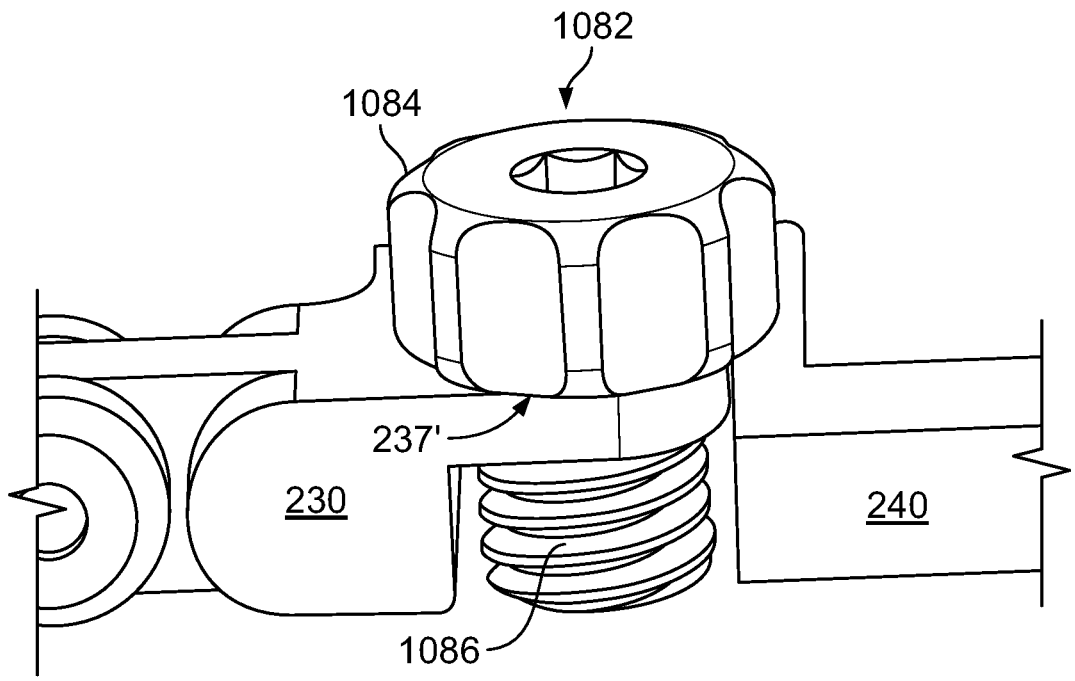
Figure 10D:
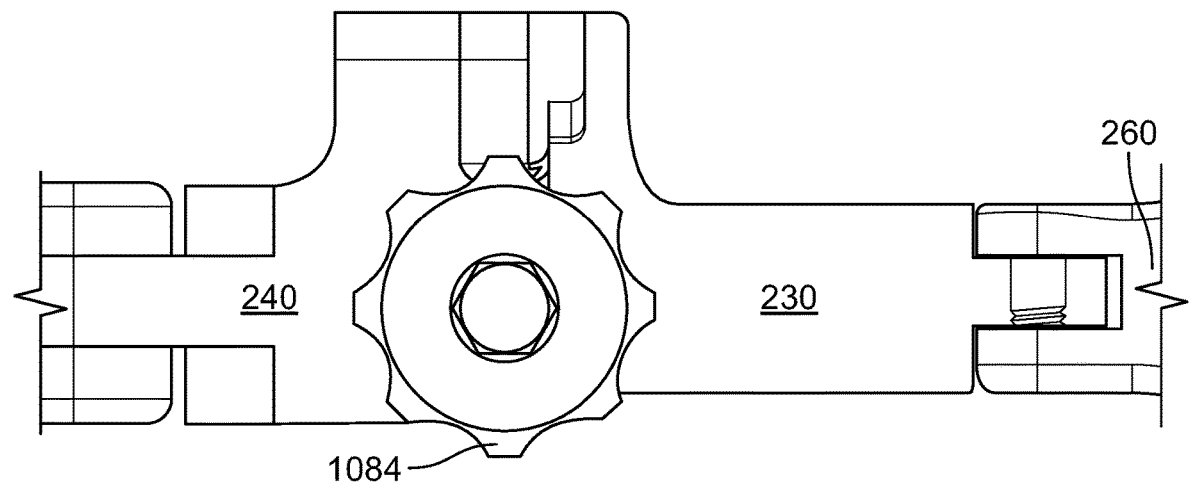
Figure 10E:
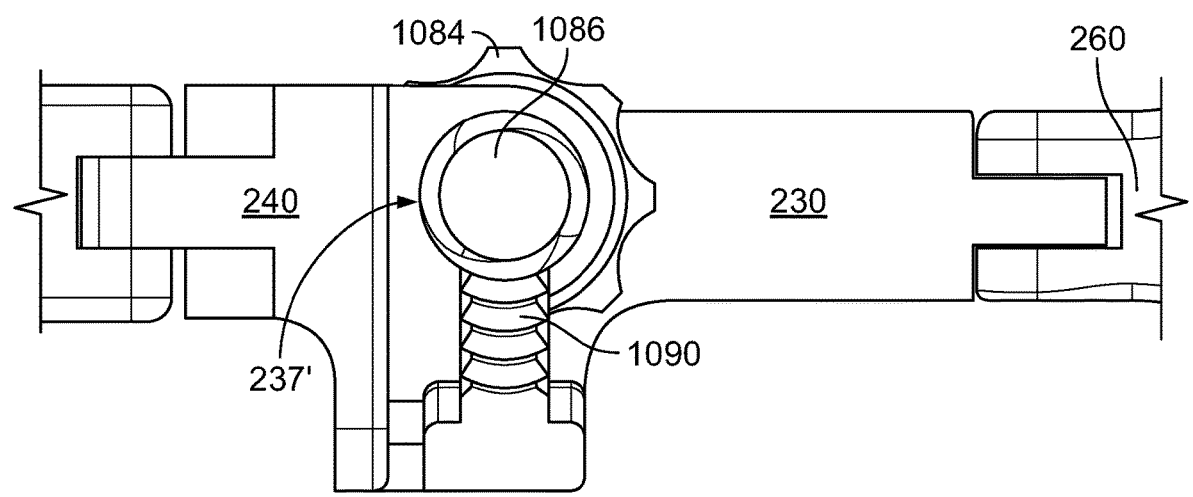

Referring now to FIGS. 8A and 8B, another embodiment of a side-load connector suitable for implementing the side-load connector 260 of FIGS. 1A-1C is shown. The side-load connector 800 of FIGS. 8A and 8B may include a housing 810 having an upper surface 812, a lower surface 814 with a serrated portion or teeth 816, and a side surface or sidewall 818 adjoining the upper surface 812 and the lower surface 814. A proximal end 820 of the side-load connector 800 may include one or more barrels 822 which may interleave with one or more barrels 245 of the distal arm portion 240 (see, FIGS. 1A-1C) to form a hinge in a manner similar to the hinge 250 discussed above in regarding to FIGS. 1A-1C.

As shown, the side-load connector 800 further includes a port 830, a sidewall opening 840, a cam 850, a button 860, a first spring 870, and a second spring 880. The port 830 provides a cylindrical aperture that passes through the upper surface 812 and lower surface 814. While the port 830 is generally cylindrical, the sidewall opening 840 passes through the sidewall 818 of the housing 810 to the port 830. As such, an inner wall 832 of the port 830 is broken by the sidewall opening 840. Due to such discontinuity in the inner wall 832, the inner wall 832 only partially circumscribes the port 830, thus permitting loading the attachment post 330 via the sidewall opening 840. Moreover, the port 830 has a diameter that is slightly larger than the diameter of the attachment post 330. As such, the inner wall 832 may closely mate with the longitudinal sidewall 334 of the attachment post 330 when the attachment post 330 is loaded into the port 830.

As shown, the cam 850 is pivotably coupled between the upper surface 812 and the lower surface 814 via a pin 852 positioned adjacent the sidewall opening 840. The pin 852 permits the cam 850 to rotate about a pivot point, between an opened position (not depicted) and a closed position depicted in FIGS. 8A and 8B. When in the closed position, the cam 850 includes a first distal portion 856, a second distal portion 858, and a third distal portion 859 that extend radially from the pin 852 and into the sidewall opening 840. The first distal portion 856 may generally engage a groove 338, 340 of a loaded attachment post 330 when the cam 850 is in the closed position. The first distal portion 856 provides a circular surface with respect to the pivot axis of the pin 852. As such, while the cam 850 rotates between opened and closed positions, the first distal portion 856 generally maintains the same distance between itself and the opposite inner wall 832 of the port 830. In one embodiment, such distance is slightly larger than the diameter of the grooves 338, 340. As such, the first distal portion 856 may slid along a groove 338, 340 past a loaded attachment post 330.

The second distal portion 858 may generally provide an inwardly tapered surface. When the cam 850 is in the closed position, such tapering may aid a practitioner in loading an attachment post 330 of a retractor blade 330 into the port 830 as described below. The curvature of the third distal portion 859 may generally match the radial curvature of the inner wall 832 of the port 830. When the cam 850 is in the released position, the third distal portion 859 aligns with the attachment post 330. Thus, in the released position, the third distal portion 859 effectively extends the inner wall 832 and closely mates with the sidewall surface 332 of the attachment post 330. The third distal portion 859, however, does not engage grooves 338, 340 of a loaded attachment post 330. As such, when in the released position, the cam 850 permits longitudinal extraction of the attachment post 330 from the port 830.

As shown, the second spring 880 may be positioned opposite the button 860 to bias the button 860 and the integrated cam 850. In particular, the second spring 880 biases the cam 850 away from the released position toward the closed position. From the closed position of FIGS. 8A and 8B, the button 860 may be pressed into the housing 810 to cause the button 860 to rotate the cam 850 to the released position. As shown, the button 860 extends from a portion of the cam 850 that is radially opposite the first distal portion 854. Pressing the button 860, thus, forces the cam 850 to rotate the first distal portion 854 of the cam 850 outwardly away from the port 830 and toward the released position. In particular, in the released position, the first distal portion 854 disengages a groove 338, 340 of a loaded attachment post 330 due to alignment of the third distal portion 859 with the post 330. With the third distal portion 859 aligned with the attachment post 330, the attachment post 330 may be extracted from the port 830 via longitudinal movement along the port 830.

The torsion spring 870 may be coupled between a seat 817 in the housing 810 and the cam 850 to provide a biasing force to the cam 850. In particular, the spring 870 may bias the cam 850 away from the opened position and toward the closed position. Accordingly, when no external forces are applied to the cam 850, the spring 870 places the cam 850 in the closed position.

When side loading the attachment post 330, the practitioner may press the attachment post 330 against the second distal portion 858, which provides a tapered opening toward the port 830. As the attachment post 300 continues to travel toward the port 830, the attachment post 300 overcomes the biasing force of the spring 870, thus causing the cam 850 to rotated toward the opened position. When the attachment post 300 is loaded into the port 830, the attachment post 300 is positioned beyond the second distal portion 858 and comes in contact with the first distal portion 856. Due to the first distal portion 856 maintaining a distance to the opposite inner wall of the port 830 that is slightly large that the diameter of the grooves 338, 340, the spring 870 causes the cam 840 to snap back to the closed position once the attachment post 330 is loaded and one of the grooves 338, 340 is aligned with the cam 840.

To unload retractor blade 300, the practitioner may press the button 860 into the housing 810 to place the cam 840 in a released position. Once in the released position, the practitioner may withdrawal the attachment post 330 from the port 830 by pulling the attachment post 330 longitudinally away from the bottom surface 814 of the housing 810.

Referring now to FIGS. 9A and 9B, another embodiment of a side-load connector suitable for implementing the side-load connector 260 of FIGS. 1A-1C is shown. The side-load connector 700' of FIGS. 9A and 9B generally operates in a manner similar to side-load connector 700 of FIGS. 7A and 7B. As such, similar aspects of FIGS. 9A and 9B are provided with the same reference labels as FIGS. 7A and 7B.

The main difference between the connectors is the location of the sidewall opening 740. The sidewall surface 718 of FIGS. 7A, 7B, 9A, and 9B generally comprises a back sidewall 718B pivotably coupled to a retractor arm 200 and a front sidewall 718F opposite the back sidewall 718B. The sidewall surface 718 further comprises a left sidewall 718L adjoining the front sidewall 718F and the back sidewall 718B and a right sidewall 718R opposite the left sidewall 718L and adjoining the front sidewall 718F and the back sidewall 718B. The sidewall opening 740 of the connector 700 in FIGS. 7A, and 7B is through the left sidewall 718L. The sidewall opening 740 of the connector 700' in FIGS. 9A and 9B is through the front sidewall 718F. Generally speaking, the sidewall opening of the disclosed connectors may be position anywhere along the left, right, and front sidewalls.

Moreover, FIGS. 9A and 9B depict the side-load connector 700' with a single cam 750. However, as shown in FIGS. 11A-11D, the side-load connector may be implemented as a dual cam design in which the side-load connector includes a cam 750 positioned to each side of the opening 740.

Referring now to FIGS. 10A-10E, an alternative embodiment of angle adjustment assembly that may replace the angle adjustment assembly 280 of the retractor system 10 shown in FIGS. 1A-1C. The angle adjustment assembly 1080 may adjust a relative angle between the proximal arm portion 230 and the distal arm portion 240. In particular, the angle adjustment assembly 1080 may comprise a worm drive 1081 via which an operator can cause the distal arm portion 240 to pivot about axis 226 of the hinge 220. To this end, the worm drive 1081 may include a worm screw 1082 having a handle 1084 at a proximal end of a threaded shaft 1086. A distal end of the threaded shaft 1086 may pass through a non-threaded aperture 237' of the proximal arm portion 230. In particular, the proximal arm portion 230 may retain the threaded shaft 1086 within the non-threaded aperture 237' such that the worm screw 1082 is longitudinally affixed to the proximal arm portion 230, but rotatable about longitudinal axis of the shaft 1086.

The worm drive 1081 may further include a worm gear 1090. The worm gear 1090 may be positioned along a proximal end 242 of the distal arm portion 240 such that teeth 1092 of the worm gear 1090 mesh with threads of the worm screw 1082. Rotation of the worm screw 1082 via the handle 1084 in a first direction may adjust or force the distal arm portion 240 to pivot about the axis 226 in a clockwise direction. Conversely, rotation of the worm screw 1082 a second direction opposite the first direction may adjust or force the distal arm portion 240 to pivot about the axis 226 in a counter-clockwise direction.

Referring now to FIGS. 11A-11D, an alternative embodiment of angle adjustment assembly that may replace or be used in addition to the angle adjustment assembly 280 of the retractor system 10 shown in FIGS. 1A-1C or the angle adjustment assembly 1080 of the retractor system shown in FIGS. 10A-10E. As shown in FIGS. 11A-D, each retractor arm 200' may include a proximal arm portion 230' and a distal arm portion 240'. Each proximal arm portion 230' may include a proximal end 232' pivotably coupled to a base portion 126 of a respective ratchet 120 via a hinge 210'. Each hinge 210' may comprise a pin 212', one or more barrels 128 of the base portion 126, and one or more barrels 233' of the proximal arm portion 230'. The barrels 128 may interleave with the barrels 233' and define a longitudinal aperture 214'. Each pin 212' may pass through a respective aperture 214' defined by barrels 128, 233', thereby pivotally coupling the proximal end 232' of the proximal arm portion 230' to its respective base portion 126.

Figure 11A:
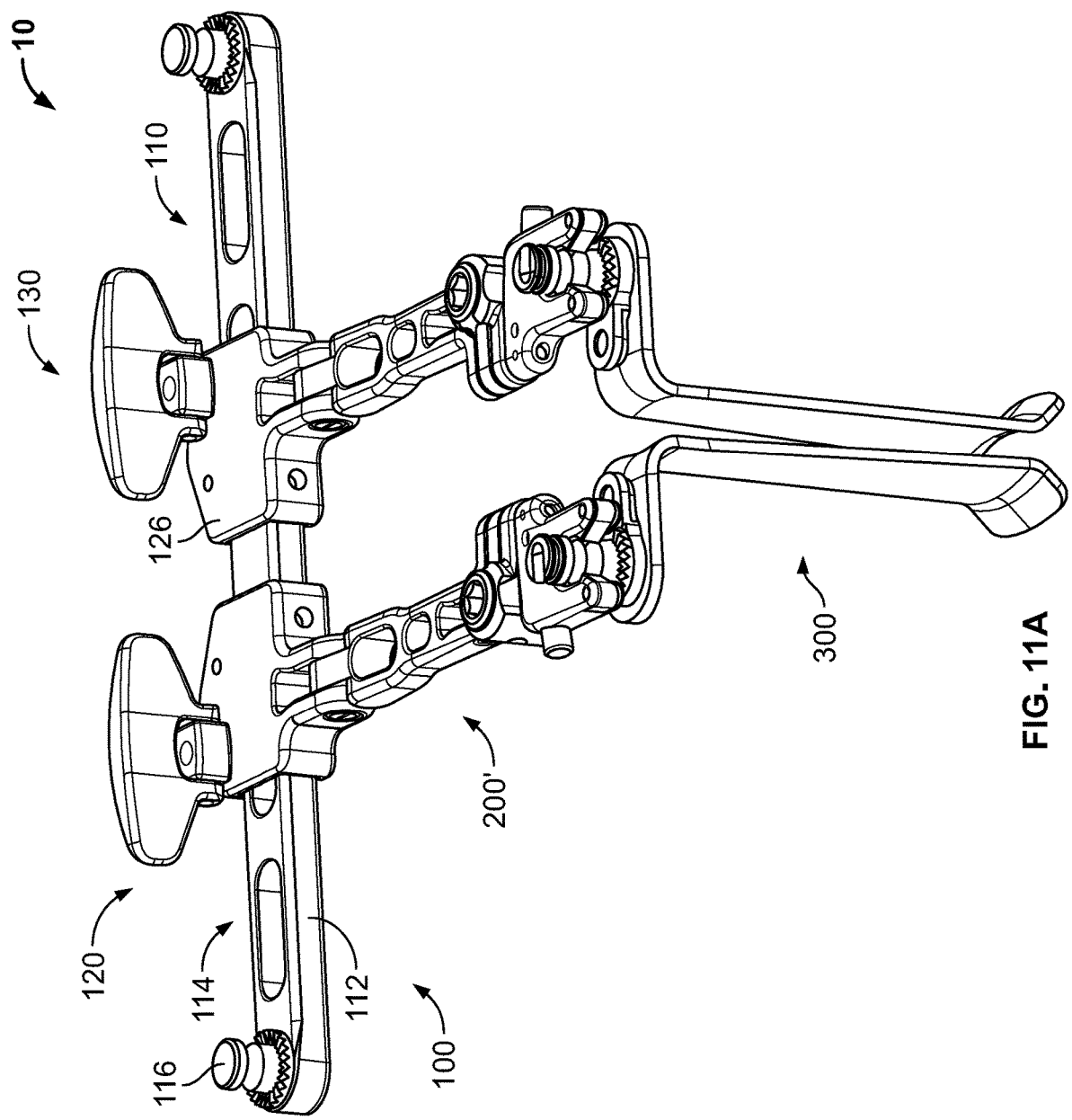
FIGS. 11A-11D depict a further embodiment of a retractor arm for the retractor system of FIGS. 1A-1C that has yet another alternative embodiment of an angle adjustment assembly in accordance with various aspects of the present disclosure.
Figure 11B:
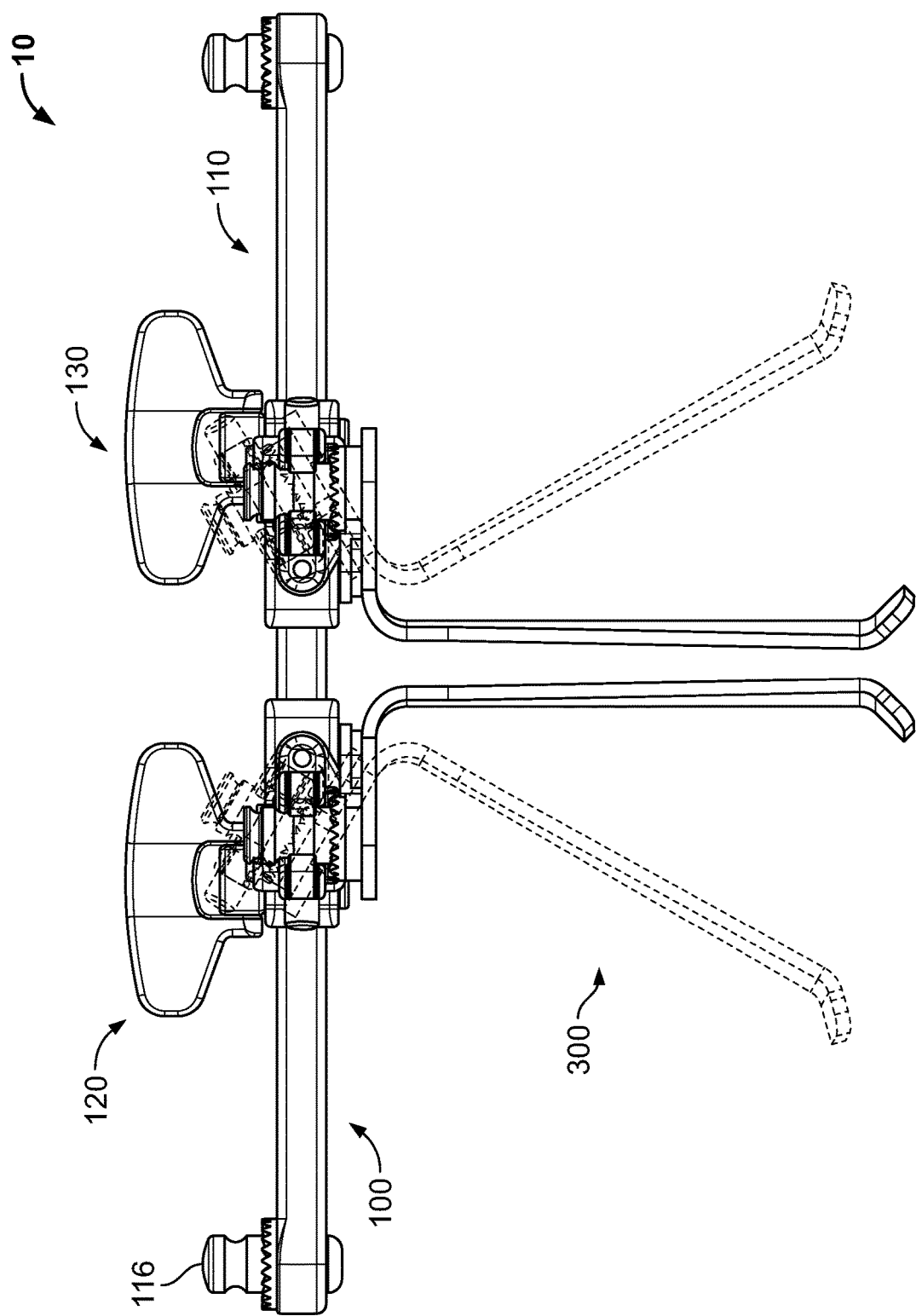
Figure 11C:
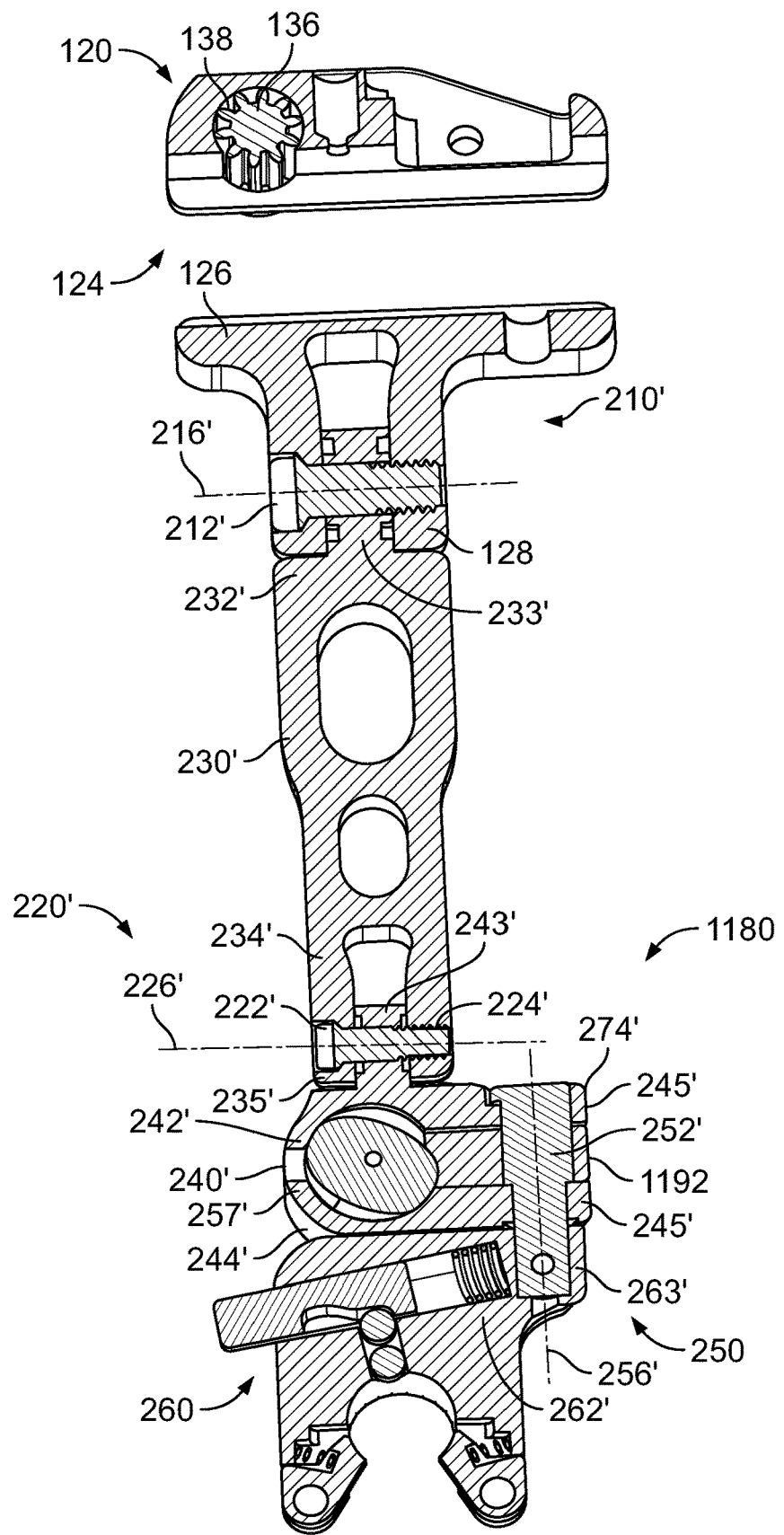
Figure 11D:
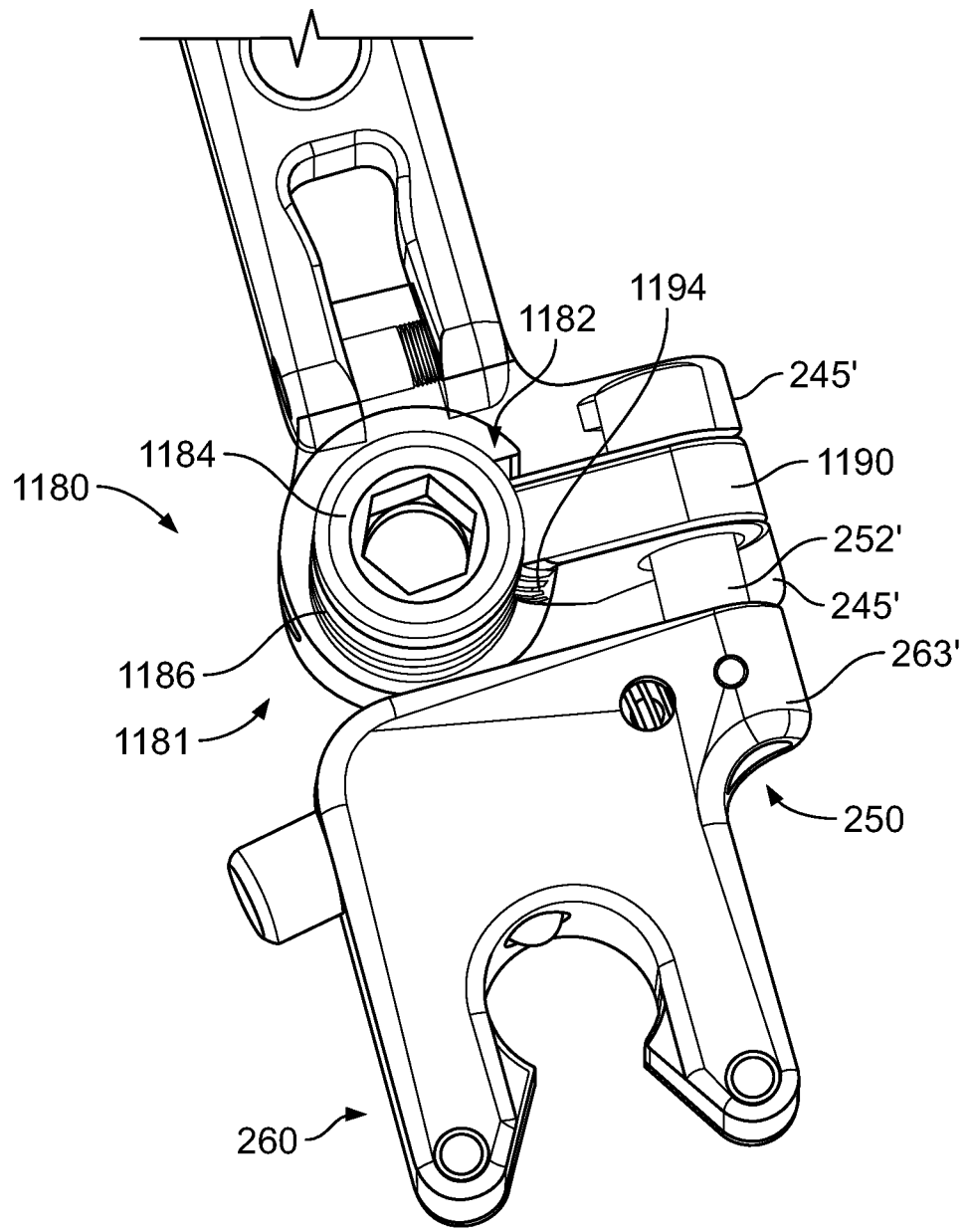

Each hinge 210' may further provide a pivot axis 216' about which the proximal arm portion 230' may pivot. As shown, each hinge 210' may provide pivot axis 216' that is coplanar with and parallel to crossbar 110. In other embodiments, each hinge 210' may orient pins 212' and barrels 128, 233' such that each axis 216' is not coplanar with and/or is not parallel to crossbar 110. Furthermore, while FIG. 11A depicts each pivot axis 216' as having the same orientation with respect to the crossbar 110, in some embodiments, the hinges 210' may distinctly orient the pivot axis 216' with respect to the crossbar 110 so as to provide each arm 200 with a pivot axis 216' that is oriented differently from the pivot axis 216' of the other arm 200.

A proximal end 242' of each distal arm portion 240 may be pivotably coupled to a distal end 234' of its respective proximal arm portion 230' via a hinge 220'. Each hinge 220' may comprise a pin 222', one or more barrels 235' of the proximal arm portions 230', and one or more barrels 243' of the distal arm portion 240'. The barrels 235' may interleave with the barrels 243' and define a longitudinal aperture 224'. Each pin 222' may pass through a respective aperture 224' defined by barrels 235', 243', thereby pivotally coupling distal ends 234' of the proximal arm portions 230' to respective proximal ends 242' of the distal arm portions 240'.

As shown, each hinge 220' may provide a pivot axis 226' about which the distal arm portion 240' may pivot. As shown, the hinges 220' may provide pivot axes 226' that are coplanar with and parallel to crossbar 110. In other embodiments, the hinges 220' may orient pins 222' and barrels 235', 243' such that each axis 226' is not coplanar with and/or is not parallel to crossbar 110. Furthermore, while FIG. 11A depicts each pivot axis 226' as having the same orientation with respect to the crossbar 110, in some embodiments, each hinge 220' may distinctly orient its pivot axis 226' with respect to the crossbar 110 so as to each 200' provides its pivot axis 226' oriented differently from the pivot axis 226' of the other arm 200'.

A proximal end 262' of each side-load connector 260' may be pivotably coupled to a distal end 244' of its respective distal arm portion 240' via a hinge 250'. Each hinge 250' may be defined by one or more barrels 263' of the side-load connector 260', one or more barrels 245' of the distal arm portion 240', one or more barrels 1192 of a worm gear 1190, and a pin 252'. The barrels 245', 263', 1192 may interleave and align to define a longitudinal aperture 274'. Each pin 252' may pass through the aperture 254' defined by barrels 245', 263', thereby pivotally coupling distal ends 244' of the distal arm portions 240' to respective proximal ends 262' of the side-load connectors 260'.

Each hinge 250' may provide a pivot axis 256' about which the side-load connector 260' may pivot. As shown, each hinge 250' may provide pivot axes 256' that is perpendicular to crossbar 110. In other embodiments, each hinge 250' may orient pins 252' and barrels 245', 263' such that each axis 256' is not perpendicular to crossbar 110'. Furthermore, while FIG. 11A depicts each pivot axis 256' as having the same orientation with respect to the crossbar 110, in some embodiments, each arm 200' may distinctly orient its pivot axis 256' with respect to the crossbar 110' so as to orient its pivot axis 256' differently from the pivot axis 25' of the other arm 200'.

Finally, the angle adjustment assembly 1180 may engage the distal arm portion 240' and the side-load connector 260' to adjust a relative angle between the distal arm portion 240' and the side-load connector 260'. In particular, the angle adjustment assembly 1180 may comprise a worm drive 1181 via which an operator can cause the side-load connector 260' to pivot about axis 256' of the hinge 250'. See, e.g., FIG. 11D. To this end, the worm drive 1181 may include a worm screw 1182 having a head 1184 at a proximal end of a threaded shaft 1186. A distal end of the threaded shaft 1186 may pass through a non-threaded aperture 257' of the distal arm portion 240'. In particular, the distal arm portion 240' may retain the threaded shaft 1186 within the non-threaded aperture 257' such that the worm screw 1182 is longitudinally affixed to the distal arm portion 240', but rotatable about longitudinal axis of the shaft 1186.

The worm drive 1181 may further include a worm gear 1190. As shown, the worm gear 1190 may include teeth 1194 that mesh with threads of the worm screw 1182. Moreover, the worm gear 1190 may be affixed to the proximal end 262' of the side-load connector 260' via pin 252' such that rotation of the worm screw 1182 via the head 1184 in a first direction may pivot the worm gear 1190 about the axis 256' in a clockwise direction, thereby causing the side-load connector 260' to rotate about the axis 256' due the side-load connector 260 being affixed to the worm gear 1190 via pin 252'. Conversely, rotation of the worm screw 1182 in a second direction opposite the first direction may adjust or force the side-load connector 260' to pivot about the axis 256' in a counter-clockwise direction.

In some embodiments, the angle adjustment assembly 1180 may provide stops that prevent rotating the side-load connectors 260' toward one another past a first stop position at which the retractor blades 300 are parallel to one another and perpendicular to the crossbar 110. See, e.g., FIG. 11B. As further shown in FIG. 11B, the angle adjustment assembly 1180 may further ensure that distal ends of the retractor blades 300 do not delve deeper into an incision as the retractor blades 300 are rotated away from the first stop position. As further shown in FIG. 11B, a vertical displacement between the distal ends of the retractor blades 300 and the crossbar 110 decreases as the angle adjustment assembly 1180 rotates the retractor blades 300 away the from the first stop position.

FIGS. 11A-11D depict the angle adjustment assembly 1180 with a worm drive 1181. However, other embodiments may implement the angle adjustment assembly 1180 via other mechanisms. For example, the angle adjustment assembly 1180 may be implemented in a manner similar to the angle adjustment assembly 280 of FIGS. 1A-1C. In particular, the worm drive 1181 may be replaced with the thumb screw, ball, and socket implementation of FIGS. 1A-1C.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. For example, the disclosed side-load connectors and retractor blades have been generally described with serrated surfaces or teeth which lock or prevent a loaded retractor blade 300 from rotating about axis AA of the attachment post 330. Such side-load connectors and/or retractor blades may be implemented without such serrated surfaces for environments where preventing such rotation or swivel is not needed or desired. Therefore, it is intended that the present invention not be limited to the particular embodiment or embodiments disclosed, but that the present invention encompasses all embodiments falling within the scope of the appended claims.

What is claimed is:

1. A side-load connector for use with a retractor blade having an attachment post, the side-load connector comprising:

a connector upper surface, a connector lower surface, and connector sidewalls adjoining the connector upper surface and the connector lower surface;

a port that passes through the connector upper surface and the connector lower surface;

an opening in the connector sidewalls that permits loading of the attachment post of the retractor blade by permitting lateral passage of the attachment post through the connector sidewalls and into the port;

a cam pivotably coupled between the connector lower surface and the connector upper surface;

a spring that applies a biasing force on the cam that biases the cam to a closed position in which the cam extends into the opening and prevents unloading the attachment post from the port via the opening; and a lock comprising a push button, one or more bearings, and a second spring configured to apply a second biasing force that biases the lock toward a locked position;

wherein, when in the locked position, the lock engages a groove of the attachment post loaded in the port and prevents longitudinally sliding the attachment post along the port in a direction away from the connector lower surface;

wherein the push button has a ramped recess positioned to receive a bearing of the one or more bearings, the push button movable between a locked position in which a shallower portion of the ramped recess aligns with the bearing and a released position in which a deeper portion of the ramped recess aligns with the bearing;

wherein the second spring is configured to bias the push button to the locked position causing the shallower portion to press against the bearing and urge the one or more bearings to engage the groove of the attachment post loaded in the port; and wherein, when the push button is moved to the released position by an external force, the deeper portion aligns with the bearing and permits the one or more bearings to disengage from the groove of the attachment post.

2. The side-load connector of claim 1, further comprising:

a connector back sidewall configured to be coupled to a retractor arm, a connector front sidewall opposite the connector back sidewall, and a connector right sidewall adjoining the connector back sidewall and the connector front sidewall;

wherein the opening is opposite the connector right sidewall, permitting loading of the attachment post via a left side of the side-load connector.

3. The side-load connector of claim 1, further comprising:

a connector back sidewall configured to be coupled to a retractor arm, a connector front sidewall opposite the connector back sidewall, and a connector left sidewall adjoining the connector back sidewall and the connector front sidewall;

wherein the opening is opposite the connector left sidewall, permitting loading of the attachment post via a right side of the side-load connector.

4. The side-load connector of claim 1, comprising:

a connector back sidewall configured to be coupled to a retractor arm, a connector left sidewall adjoining the connector back sidewall, and a connector right sidewall opposite the connector left sidewall and adjoining the connector back sidewall;

wherein the opening is opposite the connector back sidewall, permitting loading of the attachment post via a front side of the side-load connector.

5. A retractor system, comprising:

a self-retaining retractor comprising a crossbar and a retractor arm comprising a proximal end coupled to the crossbar via a ratchet;

a retractor blade comprising a retractor body, an attachment post extending from the retractor body, and a blade extending from the retractor body; and a side-load connector coupled to the retractor arm, the side-load connector comprising a connector upper surface, a connector lower surface, connector sidewalls adjoining the connector upper surface and the connector lower surface, and a lock comprising a push button, one or more bearings, and a second spring configured to apply a second biasing force that biases the lock toward a locked position;

wherein a port passes through the connector upper surface and the connector lower surface;

wherein an opening in the connector sidewalls permits loading of the attachment post by permitting lateral passage of the attachment post into the port;

wherein a cam of the side-load connector is pivotably coupled between the connector lower surface and the connector upper surface; and wherein a spring applies a biasing force on the cam that biases the cam to a closed position in which the cam extends into the opening and prevents unloading the attachment post from the port via the opening;

wherein, when in the locked position, the lock engages a groove of the attachment post loaded in the port and prevents longitudinally sliding the attachment post along the port in a direction away from the connector lower surface;

wherein the push button has a ramped recess positioned to receive a bearing of the one or more bearings, the push button movable between a locked position in which a shallower portion of the ramped recess aligns with the bearing and a released position in which a deeper portion of the ramped recess aligns with the bearing;

wherein the second spring is configured to bias the push button to the locked position causing the shallower portion to press against the bearing and urge the one or more bearings to engage the groove of the attachment post loaded in the port; and wherein the push button, when in the released position, aligns the deeper portion with the bearing, permitting the one or more bearings to disengage from the groove of the attachment post loaded in the port.

6. The retractor system of claim 5, wherein:

the connector sidewalls include a connector back sidewall coupled to the retractor arm, a connector left sidewall adjoining the connector back sidewall, and a connector right sidewall opposite the connector left sidewall and adjoining the connector back sidewall; and the opening in the connector sidewalls is opposite the connector back sidewall, permitting loading of the attachment post via a front side of the side-load connector.

7. The retractor system of claim 5, wherein the retractor arm further comprises an angle adjustment assembly configured to adjust an angle of the side-load connector with respect to the crossbar.

8. The retractor system of claim 7, wherein:

the angle adjustment assembly provides a pivot axis perpendicular to the crossbar; and actuation of the angle adjustment assembly rotates the side-load connector and the retractor blade coupled thereto about the pivot axis.

9. The retractor system of claim 8, wherein:

the angle adjustment assembly comprises a worm drive; and actuation of the worm drive rotates the side-load connector and the retractor blade coupled thereto about the pivot axis.

10. The retractor system of claim 7, wherein:

the retractor arm comprises a distal arm portion; and the angle adjustment assembly couples a proximal end of the side-load connector to the distal arm portion.

11. The retractor system of claim 7, wherein:

the retractor arm comprises a proximal arm portion and a distal arm portion;

the angle adjustment assembly couples a distal end of the proximal arm portion to a proximal end of the distal arm portion; and a proximal end of the side-load connector is coupled to a distal end of the distal arm portion.

12. The retractor system of claim 5, wherein:

the retractor body comprises a body upper surface having teeth;

the attachment post extends from the body upper surface of the retractor body;

the attachment post comprises a post top surface and a post sidewall joining the post top surface to the body upper surface;

the post sidewall comprises a first groove, a second groove displaced further from the body upper surface than the first groove, and a third groove displaced further from the body upper surface than the second groove;

the attachment post is configured to be laterally received into the port of the side-load connector via the opening through the connector sidewalls;

the first groove is configured to vertically position the attachment post in the port such that the teeth of the retractor body are engaged with teeth of the side-load connector when the cam engages the first groove;

the second groove is configured to vertically position the attachment post in the port such that the teeth of the retractor body are not engaged with the teeth of the side-load connector when the cam engages the second groove, and the third groove defines a flange for attachment of a handle assembly.

13. The retractor system of claim 12, wherein the handle assembly includes a slot configured to receive the flange of the attachment post.

14. The retractor system of claim 12, wherein:

the teeth of the body upper surface prevent the blade from swiveling about a longitudinal axis of the port when the first groove is aligned with the cam; and the teeth of the body upper surface permit the blade to swivel about the longitudinal axis of the port when the second groove is aligned with the cam.

* * * * *